(12) United States Patent
Manabe et al.

(10) Patent No.: US 8,623,210 B2
(45) Date of Patent: Jan. 7, 2014

(54) PORE DIFFUSION TYPE FLAT MEMBRANE SEPARATING APPARATUS

(75) Inventors: Sei-ichi Manabe, Kitakyusyu (JP); Chieko Seki, Kitakyusyu (JP)

(73) Assignee: Sei-ichi Manabe, Kasuya-gun, Fukuoka (JP)

( * ) Notice: Subject to any disclaimer, the term of this patent is extended or adjusted under 35 U.S.C. 154(b) by 817 days.

(21) Appl. No.: 12/224,626

(22) PCT Filed: Mar. 2, 2007

(86) PCT No.: PCT/JP2007/054055
§ 371 (c)(1), (2), (4) Date: Dec. 9, 2008

(87) PCT Pub. No.: WO2007/102427
PCT Pub. Date: Sep. 13, 2007

(65) Prior Publication Data
US 2009/0145831 A1  Jun. 11, 2009

(30) Foreign Application Priority Data

Mar. 2, 2006 (JP) .................................. 2006-055645
Mar. 23, 2006 (JP) .................................. 2006-081759
May 11, 2006 (JP) .................................. 2006-133022
May 25, 2006 (JP) .................................. 2006-144764
Jun. 15, 2006 (JP) .................................. 2006-166752

(51) Int. Cl.
*B01D 63/08* (2006.01)
*B01D 61/28* (2006.01)
*B01D 71/10* (2006.01)

(52) U.S. Cl.
USPC ................. 210/321.75; 210/321.71; 210/231; 210/500.29; 210/646

(58) Field of Classification Search
None
See application file for complete search history.

(56) References Cited

U.S. PATENT DOCUMENTS 4,581,140 A    4/1986  Manabe et al.
4,980,054 A *  12/1990 Lavender ..................... 210/90

(Continued)

FOREIGN PATENT DOCUMENTS

EP  0 582 822 A1  2/1994
JP  B1-43-1859    1/1968

(Continued)

OTHER PUBLICATIONS

Extended European Search Report dated Jun. 20, 2012 in corresponding EP Patent Application No. 12157596.3.

(Continued)

*Primary Examiner* — Krishnan S Menon
(74) *Attorney, Agent, or Firm* — Muncy, Geissler, Olds & Lowe, PLLC

(57) ABSTRACT

A pore diffusion type flat membrane separation apparatus X including a plurality of flat membranes 7 and a plurality of flat plate-like supports 1 arranged alternately with each other, each flat membrane 7 defining a plurality of pores and configured to separate a predetermined dispersed substance contained in a solution by a pore diffusion technique, each flat plate-like support 1 having a flow conduit 2 on one or both faces thereof. A ratio between a spatial volume of the flow conduit 2 and a membrane area of the flat membrane 7 is set from 0.04 to 0.4 cm. The flat plate-like support 1 includes, in at least two positions in a lateral face thereof water conduits 3 in communication with the flow conduit 2, so that flow directions of the solution in the flow conduits 2 of upper and lower flat plate-like supports 1 across the flat membrane 7 may be substantially same directions. The flat plate-like support 1 and the flat membrane 7 can be assembled with and disassembled from each other.

5 Claims, 5 Drawing Sheets

(56) References Cited

U.S. PATENT DOCUMENTS

| | | | |
|---|---|---|---|
| 5,114,581 | A | 5/1992 | Goldsmith et al. |
| 2003/0168408 | A1 | 9/2003 | Rajagopalan et al. |

FOREIGN PATENT DOCUMENTS

| | | |
|---|---|---|
| JP | A-55-14045 | 1/1980 |
| JP | A-60-183008 | 9/1985 |
| JP | B2-62-44017 | 9/1987 |
| JP | A-1-107804 | 4/1989 |
| JP | U-2-81623 | 6/1990 |
| JP | B2-46608 | 10/1990 |
| JP | A-H06-106037 | 4/1994 |
| JP | A-7-132215 | 5/1995 |
| JP | A-7-194946 | 8/1995 |
| JP | A-10-180052 | 7/1998 |
| JP | A-11-216341 | 8/1999 |
| JP | A-2005-40756 | 2/2005 |
| JP | A-2005-296937 | 10/2005 |
| JP | A-2005-349268 | 12/2005 |
| JP | A-2006-55780 | 3/2006 |

OTHER PUBLICATIONS

Extended European Search Report dated Jun. 20, 2012 in corresponding EP Patent Application No. 12157597.1.

Berg, Jack H., "Filtration and Purification of Plating and Relating Solutions and Effluents," Metal Finishing, Elsevier, New York, NY, US, Jan. 1, 2001, vol. 99, pp. 710, 712, 714, 716, 718, 720-728.

*Investigations about Separating Membranes*, vol. 1, vol. 2, vol. 3, Osaka Chemical Marketing Center, 1980, 1981, 1982. (Japanese language; mentioned on p. 6, 7 and 15 of Specification as "Non-Patent Document 1").

Kyoritsu Shutsugan, *Physical Properties of Polymers, complied by the Society of Polymer Science*, Japan, p. 50, 1995. (Japanese language, mentioned on p. 6, 7 and 15 of Specification as "Non-Patent Document 2").

Manabe et al., *Dynamic Mechanical Absorptions Observed for Regenerated Cellulose Solids in the Temperature Range from 280 to 600 K*, The Society of Polymer Science, Japan, vol. 18, No. 1, pp. 1-14, 1986. (Mentioned on p. 7, 15 of Specification as "Non-Patent Document 3").

International Search Report dated Jun. 5, 2007 in corresponding PCT patent application No. PCT/JP2007/054055 (and English translation).

International Preliminary Report on Patentability dated Oct. 23, 2008 in corresponding PCT patent application No. PCT/JP2007/054055 (and English translation).

Office Action issued Jan. 31, 2013 in corresponding JP Application No. 2008-503826 (and partial English translation).

Oya, Haruhiko "Reverse Osmosis and Ultrafiltration II, Application: Membrane Technique Handbook." Japan, Saiwai Shobo Co., Jun. 30, 1978.

Office Action dated Nov. 1, 2012 in corresponding JP Application No. 2008-503826 (and partial English translation).

\* cited by examiner

PORE DIFFUSION TYPE FLAT MEMBRANE SEPARATING APPARATUS

CROSS REFERENCE TO RELATED APPLICATIONS

This application is a U.S. national stage application of PCT/JP2007/054055 filed on Mar. 2, 2007, and claims priority to, and incorporates by reference, Japanese Patent Application Nos. 2006-055645 filed Mar. 2, 2006, 2006-081759 filed Mar. 23, 2006, 2006-133022 filed May 11, 2006, 2006-144764 filed May 25, 2006, and 2006-166752 filed Jun. 15, 2006.

TECHNICAL FIELD

The present invention relates to a pore diffusion type flat membrane separation apparatus for effecting solid-liquid separation through utilization of a pore diffusion mechanism of a flat membrane. The invention relates also to a flat membrane concentration apparatus using a flat membrane, a regenerated cellulose porous membrane as a flat membrane, and to a method of inspecting a flat membrane.

BACKGROUND ART

Pore Diffusion Type Flat Membrane Separation Apparatus

Examples of the conventional membrane separation apparatuses for liquid separation include a hollow fiber membrane module, a tubular membrane module, a flat membrane module, a spiral membrane module, a pleated membrane module, and so on, all of which rely mainly on filtration separation technique. Further, with these modules, for retention of the membrane, a portion of the membrane and a support are adhesively bonded to each other by means of a resin or the like, Especially, when its effective filtering area exceeds 0.1 $m^2$, the vessel (housing) or the support needs to be formed of stainless steel in order to withstand an transmembrane pressure difference, so that the mode tends to be hardly portable or tends to be configured as a hollow fiber module having a portion of the membrane being adhesively fixed by means of a resin or the like.

In the case of the membrane filtration technique, provision of transmembrane pressure difference is essential. As this pressure is born mainly by the outermost layer of the module in the case of the flat membrane module, its outermost layer is added with a reinforcing material, which addition makes observation inside the module difficult.

Also, in the case of the membrane filter technique, clogging of the pores inside the membrane occurs, which makes regeneration of the membrane difficult. Further, as the separation by the membrane filter technique relies on the pore diameter of the membrane, if the size of the molecules to be separated is small, the average pore diameter of the separating membrane too needs to be small correspondingly, so that the filtering amount per effective filtering area becomes correspondingly small thus becoming even more liable to invite the clogging phenomenon.

Notwithstanding the above, in the case of the above module having adhesive bonding with resin, as a portion of the membrane and the support are adhesively bonded with each other for retention of the membrane, if the membrane or the module portion alone has been damaged, replacement of such damaged portion alone was difficult.

Further, in the case of the module using the membrane filter technique, in effecting filtering separation, due to the readiness of clogging in the membrane, it is difficult to maintain stable membrane filtering performance. Moreover, such module is configured generally for one time use only, in sanitary point of view. As a result, its manufacturing costs would be high.

Flat Membrane Concentration Apparatus

As the technique for concentrating a certain substance in a solution, there have been implemented such methods as evaporation, concentration, freeze-drying, precipitation, adsorption, etc. Moisture elimination relying on evaporation or concentration does not involve any phase separation and also consumes a great amount of energy.

Further, this concentration results in loss of activity of a biologically active agent such as a protein.

The precipitation technique requires addition of at least a third component and the concentrated component resulting therefrom is in the form of solid, as it happens with the freeze-drying technique.

The precipitation method provides selective concentration, but involves dilution through desorption and requires high costs.

On the other hand, the concentration technique using membrane is capable of concentration under mild conditions and with energy saving. Hence, there is expectation for application of this technique in the biochemical industry in particular.

The concentration technique using membrane is implemented generally by filtration. Due to a positive relationship existing between the filtration rate and the transmembrane pressure difference, the filtration concentration is effected, with increased transmembrane pressure difference. For obtaining such increase of transmembrane pressure difference, the membrane is to be configured as a hollow fiber membrane or a support is to be employed in the case of a flat membrane. However, with such increase of transmembrane pressure difference, there occurs concentration of polymer component on the membrane surface, which leads to reduction in the filtration rate and reduction in the collection ratio.

In order to increase the collection ratio, a flat membrane module is more advantageous, as the membrane module, in principle than a hollow fiber module. That is, the flat membrane module allows assembly and disassembly of the module, thus allowing elimination(?) and recovery elimination(?) of the membrane portion alone.

Some conventional examples of flat membrane concentration apparatus include a flat plate type, which has the simplest apparatus construction and a pipe type, a spiral type, a pleated type, a rotary membrane type. In the case of flat membrane filtration, some device or arrangement will be needed for withstanding the transmembrane pressure difference.

Such device or arrangement for solving these problems relating to pressure resistance and membrane charge density often comprises a complicated and large structural feature of the apparatus, and a metallic material is generally employed as the material for forming the support. Hence, in the module of the apparatus, the respective members constituting the same are formed integral or have shapes which cannot be disassembled easily, so that the transportation, installment, cleaning of the support or liquid inlet/outlet connectors, replacement of expendable parts or the membrane would be difficult. For this reason, commercial application of a concentrating apparatus using flat membrane has been believed impossible.

In the context of the present invention, the term "flat membrane" refers to a membrane which has a membrane thickness of 1 μm or more and not greater than 1 mm and a ratio between the surface area of the flat membrane face and the cross section along the membrane thickness is 20 or more and whose cylinder, in case the membrane is formed like a cylinder, has a radius of 5 mm or more.

The filtration method includes a method of filtering as unfiltered stock solution is caused to flow parallel with the membrane surface (parallel filtration, cross-flow filtration, or tangential flow filtration) and a method of filtering without such flowing of stock solution (vertical filtration or dead-end filtration).

As the membrane concentration method using hollow fibers, the parallel filtration method is normally employed. Whereas, in the case of flat membrane, both the parallel filtration and the vertical filtration are employed. In the case of the parallel filtration, the support is normally not used on the pressurizing side thereof. The concentration ratio is defined as a ratio between the concentration in the collected liquid and the concentration in the stock solution.

In the case of the membrane concentration by parallel filtration not using any support, the membrane is set vertical for effective utilization of the membrane face. In this, however, if the stock solution contains diffused substance at a high concentration, this diffused substance will be precipitated in the lower layer, thus leading to disadvantageous reduction in the effective filtering area of the membrane.

Further, at the time of collection of concentrated liquid, gas needs to be fed therein in reversed vertical direction. And, as a problem commonly suffered by the membrane concentration technique, with increase in the concentration ratio during membrane concentration, there occurs increase in the osmotic pressure, so that the concentration speed will be reduced, and filtering-out of component to be collected occurs in the filtered liquid also.

Regenerated Cellulose Porous Membrane

Conventionally, the membrane separation technique is effected mainly as filtration using transmembrane pressure difference as a driving force for required substance movement. In filtration, as the processing liquid enters, as a fluid, the pores of the porous membrane, there occurs clogging of the pores and concentration polarization on the surface of the membrane, whereby in association with reduction in the average pore diameter of the membrane, there will occur sharp reduction in the amount of liquid which can be treated by the membrane.

Moreover, as the filtration speed varies in proportion to the $4^{th}$ or $2^{nd}$ power of the average pore diameter (when the porosity remains the same), when the average pore diameter is reduced, the filtration speed decreases sharply.

The membrane separation technique which allows separation under mild conditions is beginning to find more and more applications in the field of biotechnology using biological resources as materials. In particular, in the case of the manufacture of biological medical products or the refining of food products, the membrane separation technique has become an absolutely needed separating/refining measure. In these fields, the membrane separation technique is employed for removal of infectious particles (prions, viruses, bacteria, etc.), thus playing an important role for safety measure.

In the context of the present invention, the term "membrane separation technique" refers to:

(1) a membrane filter technique which utilizes a pressure difference between front and back faces of the membrane as a driving force for substance transport to cause a hydrodynamic force, so as to effect substance separation through relationship between the pore diameter and the particle diameter; and (2) a pore diffusion technique which uses a concentration difference between two kinds of liquid via a membrane as a driving force for substance transport and effects separation not by causing any liquid flow, but by utilizing thermal mobility difference of molecules of the substance (so-called Brownian motion) as well as through the sieving effect caused due to the relationship between the pore diameter of the membrane and the particle diameter; and (3) a diffusion dialysis technique which uses a concentration difference via a semipermeable membrane as a driving force for substance transport and effects molecule separation with using an affinity difference between the membrane and the substance and a difference between the size of space of free volume caused by thermal mobility (micro Brownian motion) of the polymer material forming the membrane and the size of the substance particle.

Diagrams of the pore diffusion technique are shown in FIGS. 9-10.

FIG. 9 shows a schematic section of a membrane used in the pore diffusion, taken parallel to the flat membrane face. A plurality of structures as shown are stacked in the form of layers along the membrane thickness direction, whereby the membrane is configured as a multi-layered structure.

FIG. 10 illustrates separation based on a mechanism pore diffusion of a solution containing particles of albumin, virus and prions as particles to be removed. Albumin particles having the minimal particle diameter can pass most of the pores present in the membrane, so that these particles pass the membrane along the diffusing direction. Whereas, as there exist almost no pores of diameters which allow passage therethrough of the viruses or prions having larger diameters than albumin, it takes a long time for their passage through the pores.

Membranes employed in the membrane separation technique can be classified, in terms of forms thereof, between a hollow fiber membrane and a flat membrane. In the case of the hollow fiber membrane, the support for membrane is not needed, but as the vessel and the hollow fibers are formed integral as the membrane separator, replacement of the membrane alone is not possible, so that the entire vessel needs to be replaced.

On the other hand, in the case of the flat membrane, the support for supporting the membrane is needed, so that there is the problem of enlargement of the module per unit membrane area and enlargement in the filling liquid amount. However, as replacement of the membrane alone is possible, cost of membrane separation can be reduced.

As the methods of manufacturing separating membrane, there are e.g.: (1) micro-phase separation technique, (2) etching technique using solvent, (3) a technique utilizing formation of pores in association with extension (see, Non-Patent Document 1).

As the method of manufacturing a separating membrane for the purpose of elimination of microparticles, the micro phase separating technique is suitable. Here, the term microphase separating technique means the following methods (see e.g. Non-Patent Document 2).

Namely, in the wet or dry type membrane manufacturing method, the membrane forming stock solution is under a uniform one-phase liquid condition. During flow extending operation in the case of the flat membrane or during the fiber forming process in the case of the hollow fiber membrane, there occurs phase separation into polymer thick phase and thin phase. In this, with the phase separation, growth of primary particles occurs probably after formation of nucleus of a few nm. Further growth to the secondary particles (from 50 to a few hundreds nm in diameter) occurs mainly through association/fusion of the primary particles. These secondary particles are relatively stable, so this condition is referred to as micro-phase separation condition. The micro-phase separation method refers to a method in which the primary particles and the secondary particles are coagulated and stacked to be formed continuous with each other, thus forming a porous membrane.

As a method of manufacturing regenerated cellulose, there is known a method comprising: adding an inorganic salt such as water glass or an organic solvent such as acetone into a cuprammonium regenerated cellulose stock solution; causing micro-phase separation by either wet or dry method; and removing salt or metal remaining after solidification of the membrane, with an acid (see Patent Documents 1 and 2). With this method, the phase separation requires long time, so that it has been industrially difficult to obtain the membrane thickness of 200 µm or more and the porosity of 80% or more. And, it has been difficult also to obtain the average pore diameter of 10 nm or less.

On the other hand, there is known a method of manufacturing a porous membrane from a cellulose derivative, e.g. cellulose acetate by the micro phase separation technique (see Non-Patent Document 1). It is possible, in principle, to convert a cellulose acetate porous membrane obtained by this method into a regenerated cellulose porous membrane by a saponification reaction.

With this method, however, there occurs severance of main chain, leading to significant reduction in mechanical strength. So, it has been difficult to apply this method to a porous membrane having a large porosity in particular. Further, since there occurs also a change in the pore characteristics due to the saponification treatment, there is known no practical application of regenerated cellulose membrane by combination of the micro-phase separation technique and saponification treatment.

Inside the regenerated cellulose solid, there exist a portion where intermolecular hydrogen bond has well developed and a portion where the bond has not well developed. The most developed area becomes a crystal area and it is believed that an appropriate degree of crystallinity degree is required for providing the porous membrane with shape stability.

Further, the degree of swelling of porous membrane when submerged in water strongly depends on the degree of development of intermolecular hydrogen bond. And, depending on the direction of intermolecular hydrogen bond, there occurs anisotrophy in the swelling degree. Due to this anisotrophy, there appears a change in the substance permeation function, depending on the kind of liquid, during use of the membrane, so the membrane will be deformed in use.

The development degree of intermolecular hydrogen bond is evaluated by dynamic viscoelastic temperature characteristics (see Non-Patent Document 3). In an area where the intermolecular hydrogen bond has hardly developed, dynamic absorption due to the micro-Brownian motion of cellulose molecule chain appears in the temperature range from 115 to 200° C. In an area outside the crystal area, within a region where the intermolecular hydrogen bond has most developed, the dynamic absorption due to the micro-Brownian motion of cellulose molecule chain appears in the temperature range from 285 to 305° C.

Therefore, the degree of intermolecular hydrogen bond development is defined by the following Mathematical Formula 1.

degree of intermolecular hydrogen bond development=$(T_s-T_o)/(T_{100}-T_o) \times 100 (\%)$   [Mathematical Formula 1]

In the above, $T_s$ is the temperature when the dynamic loss tangent of a sample has a value of 0.1. $T_o$ is the temperature (115° C.) when the sample of the least developed intermolecular hydrogen bond has a dynamic loss tangent value of 0.1. $T_{100}$ is the temperature (305° C.) when the sample of the most developed intermolecular hydrogen bond has the dynamic loss tangent value of 0.1.

Taking some examples of intermolecular hydrogen bond development degrees of known regenerated cellulose solid samples, the cuprammonium regenerated wardrobe fiber has values ranging from 85 to 95%. The hollow fiber for artificial kidney has values ranging from 75 to 85%. The hollow fiber for virus removal has values ranging from 45 to 55%. The flat membrane (cellophane) of viscous technique has values ranging from 45 to 60%. And, the greater this value, the greater the anisotrophy of the sample when submerged in water.

In the case of a flat membrane, when its effective membrane area is large, it is necessary to increase the dynamic strength of the support for the membrane. Therefore, stainless steel will be used as the material forming the support. As a result, the membrane separation apparatus will be heavy and not handy and will be costly as well.

If the housing of the flat membrane module is formed light-weight, inexpensive and reusable, the cost of membrane separation will be significantly reduced. And, with such reduction in the cost of membrane separation, the membrane separation technique will become applicable in any industry.

It may be said that the membrane technique used in the biomedical product industry and the food processing industry is a safety measure against microbial infections. As there is possibility of an unknown infectious substance being found in the future, it is needed to show that the safety measure is capable of reliably eliminating such unknown infectious substances also.

To this end, the membrane separation technique needs to be of some elucidated removing mechanism. In the case of elimination associated with affinity, e.g. the adsorption mechanism, it is not possible to anticipate its eliminating effect for an unknown infectious substance. So, it is necessary to minimize the eliminating effect relying on this function.

Membranes used for prevention of infection from microparticles have progressively decreasing average pore diameters.

For instance, for removal of AIDS virus, a membrane having an average pore diameter of 100 nm is employed. For removal of type B hepatitis virus, type or C hepatitis virus, a membrane having an average pore diameter of 35 nm is employed. For removal of parvovirus, a membrane having an average pore diameter of 15 nm or 20 nm is employed.

In the future, the membrane is expected to have not only the eliminating ability for viruses, but also eliminating ability of prions which are even smaller. However, with reduction in the average pore diameter, not only the treating speed is decreased, but also clogging is more likely to occur, in the case of filtration.

As the required microparticle eliminating ability, it is required that the membrane have a high eliminating ability of 4 or 5 or more as logarithmic reduction factor. If this requirement is to be satisfied by a flat membrane, the relationship between microparticle eliminating ability and the membrane structure needs to be elucidated. This relationship, however, has not yet been elucidated. As the function of membrane thickness in the case of a flat membrane, the thickness is currently designed to be 10 μm to 100 μm approximately, in order to achieve dynamic strength and handling readiness. Although it is believed that the membrane separation performance can be enhanced by sharpening the pore diameter distribution on the membrane surface, this concept hardly serves for fulfillment of the object of the present invention.

In order to increase the membrane separation speed, it is conceivable to decrease the membrane thickness and to increase the average pore diameter or porosity. In case the target of elimination of microparticles is a small particle, the average pore diameter needs to be small, as a matter of course. And, it is clear in principle that the porosity (Pr) should be increased in order to increase the membrane treatment speed under such situation.

However, increase of porosity (Pr) leads to deterioration in the dynamic characteristics of the membrane. Normally, the porosity is set from 0.6 to 0.7. In case the requirement regarding the dynamic characteristics is not so high, it becomes needed to further increase the porosity (Pr). However, no method has been proposed yet which enables a porosity (Pr) of 0.7 or more with maintaining the average pore diameter small.

Normally, the membrane module used for safety measure is subjected to a sterilization treatment, before its use. This treatment can cause a change in the configuration of the membrane. For this reason, it is needed to decide the configuration of membrane in advance, with anticipation of such change in configuration due to sterilization treatment. However, if such configuration change is isotropic and this change is minor, the designing of membrane module will become easy.

Even if there existed a membrane manufacturing method which allows setting the average pore diameter as small as 10 nm or less, the membrane thickness as large as 200 μm or more and the porosity (Pr) as large as 0.8 or more and which allows also rendering the development degree of intermolecular hydrogen bond in a multi-layered, regenerated cellulose flat membrane 40% or less, such method would suffer from limited filtering treatment amount and significantly increased membrane treatment cost, hence being not put into actual use.

Method of Non-Destructive Inspection of Flat Membrane

The membrane separation technique is important as a technique for separating substance under mild conditions. In particular, with membranes used in manufactures of biomedical products and food products, etc., it is desirable for them to additionally provide the function of eliminating infectious particles (viruses, bacteria, etc.)

In biotechnology, as microparticles contained in the raw materials, in addition to the infectious particles such as prions, viruses, bacteria, there are aggregates and modified products of proteins or the like. If these microparticles are mixed in a final product, they can cause various infectious diseases and fever.

For this reason, in the manufacturing process of a product obtained by the biotechnology, the above-described elimination of microparticles and deactivating step are needed. In particular, during the manufacturing process of biomedical products or food stuff, countermeasure against microparticles is essential.

Virus removal membranes and bacteria removal filters have been made into commercial products, already. And, there is the possibility of prion removal membrane technique appearing in the market in the near future.

As membrane separation method, the membrane filter technique, the pore diffusion technique and the diffusion dialysis technique are known.

The membrane filter technique uses a transmembrane pressure difference as a driving force for movement of substance.

The pore diffusion technique uses a concentration gradient of substance via pores of the membrane and effects separation by separation utilizing a difference in the thermodynamics (so-called Brownian motion) inherent in the substance particles per se and a sieving effect caused by the relationship between the diameter of the pores of the membrane and the diameter of the particles The diffusion dialysis technique uses a concentration difference across a semipermeable membrane as a driving force for substance movement and effects molecule separation with using an affinity difference between the membrane and the substance and a difference between the size of space of free volume caused by thermal mobility (micro Brownian motion) of the polymer material forming the membrane and the size of the substance particle.

In the manufacturing process of biomedical products, a virus eliminating membrane is being used in the filtration technique.

Here, the term virus eliminating membrane refers to a membrane which has (1) a virus eliminating ability represented by a logarithmic elimination coefficient of 4 or more (that is, the number of virus is 1 or less in the treated solution, relative to $10^4$ viruses); (2) a sieving mechanism as the virus eliminating mechanism; and (3) reproducibility in its eliminating ability.

For virus removal membrane, bacterial removal membrane and prion removal membrane expected to appear in the future, there is imposed an obligation to effect an integrity test on a used membrane. That is, during actual use of the membrane, a user of the membrane is obliged to carry out a test to show the membrane retaining ability higher than a predetermined eliminating ability.

The integrity test means a test for the user of the membrane to confirm that the used membrane has been under a condition where the membrane provided the originally intended membrane function.

As the membrane integrity test, there have been proposed two kinds of methods, i.e. the direct method and the indirect method.

The direct method refers to a testing method in which a microparticle having a certain predetermined size is taken as a model substance of a virus of approximately equal size, and the microparticle eliminating ability of the membrane is determined, with using an aqueous solution containing such microparticles dispersed therein. The microparticles actually used are gold colloidal particles (see, e.g. Patent Document 3).

The eliminating ability by filtration is determined and it is checked to see if the determined value is greater than a preset value.

With this method, as the eliminating ability of the membrane for particles is directly determined, the method is clear in principle. And, this method is superior as an integrity testing method for a membrane having an eliminating function based on size. In the case of inspection by this method, however, as the gold colloidal particles remain within the membrane after the inspection, the membrane after the inspection is not reusable. As it is almost impossible to completely eliminate gold within the pores, in actuality, the membrane after the testing is disposed of as a waste. The above is tantamount to that the pore structure of the membrane has been destructed by the integrity test. That is, this method, as an inspection, is a destructive inspection.

In the determination of gold particle concentration using a spectroscope, as determination of eliminating ability, there is provided representation in terms of logarithmic particle removal factor of 3 (the ratio between the concentration in the stock solution and the concentration in the treatment liquid is 1000), so the ability test by the direct method suffers the problem of insufficient precision. At present, it is believed that what is confirmed by this method is a change in the spreading in the pore diameter distribution.

Further, the gold colloidal particles tend to bond with proteins. Therefore, there is the problem that prior to effecting the integrity test, the used membrane needs to be cleaned with using e.g. caustic soda.

Here, the microparticle logarithmic removal factor is defined by the following Mathematical Formula 2.

microparticle logarithmic removal factor=log(microparticle concentration in treatment liquid/microparticle concentration after treatment) [Mathematical Formula 2]

On the other hand, in the case of the indirect method in the integrity test, the microparticle eliminating ability of the membrane is not directly determined. Rather, the method determines a physical property value relating to the pore characteristics of the membrane. And, based on this physical property value, indirectly, confirmation is made if the used membrane retains microparticle eliminating ability higher than the preset reference value or not. Moreover, in this method, the particle characteristics are not directly observed. Rather, it may be said that the method comprises an inspection method confirming mostly the interface characteristics. For this reason, it is essential that the used membrane be cleaned so as to obtain the interface characteristics within the set range.

In an actual example of the indirect method, determination is made for a membrane permeation speed of liquid when an transmembrane pressure difference is applied for a fixed period (see Patent Document 4). Or, the pore diameter is determined based on a pressure of the moment of one liquid passing pores, with application of pressure thereto, against an interfacial tension generated when the membrane is placed in contact through the pores therein with two kinds of liquid phases under equilibrium. And, when this pressure is determined to be greater than a predetermined pressure, it is possible to theoretically confirm that the size of the largest pore in the membrane is within a set pore diameter (see e.g. Patent Document 4).

All of the indirect methods proposed so far utilize the interface characteristics, so the cleaning of the membrane is essential. Further, in the case of a fluid having a large interfacial tension, such fluid applies a large negative pressure to the membrane, so that the pores thereof may be dynamically deformed or even destroyed by the integrity test. Therefore, depending on the kinds of liquid employed, it often happens that the method becomes a destructive testing method.

With the conventionally proposed direct or indirect method for integrity test, in either case, it is needed to clean the membrane after its use to enhance the accuracy of the integrity test. There are two reasons for this. Firstly, in the direct method, the microparticles employed are colloidal particles of gold, which particles are highly reactive with proteins. And, if these substances remain within the membrane, this will result in change in the entrapping ability for the gold colloidal particles within the pores. Secondly, as the membrane filter technique is employed as the membrane separation technique, on the membrane surface, the components contained in the aqueous solution to be filtered, there occurs concentration polarization, so that these components will be concentrated on the membrane surface or within the pores inside the membrane. Therefore, the cleaning of the membrane prior to integrity test is a must.

As a method of performance test for confirming microparticle eliminating performance of membrane (called "validation test" and carried out normally by the manufacturer of the membrane), there are two kinds, i.e. the direct method and the indirect method. The performance test is a test conducted by the maker of the membrane, prior to use of the membrane. The direct method includes the method using gold colloidal particles. As this is a destructive test, the test is conducted as a random inspection. That is, so far, the direct method proposed is classified as a performance test of an average value of group members in a production lot.

As the performance test in the one hundred percent inspection, only an indirect method has been proposed so far. And, as the test being one hundred percent inspection, it is required that the membrane be not destroyed by the inspection. In this testing method, for example, through utilization of a surface tension developed via pores between a gas and a liquid, determination is made for obtaining a gas permeation speed due to the maximum diameter pore or the pores adjacent thereto. As the liquid for use in this, a low boiling point liquid that has a low surface tension or lower possibility of remaining in the membrane after the inspection will be selected.

The method requires that the membrane be under dry condition and requires also that no component be dissolved from the membrane into the liquid used. In case the pore diameter is small, the transmembrane pressure difference used in this inspection method will be 10 atm or more.

Further, there has been fixedly established a belief in the art that the integrity test per se destroys the pore structure of the membrane, so there has been no attempt to reuse the membrane. And, there even exists a tendency of prohibiting reuse especially among the membrane manufacturers as the suppliers of the membranes. For this reason, it is a common practice to dispose of membranes after completion of their integrity tests.

As described above, reuse of membrane has been believed to be impossible in the field of microparticle elimination. As causes for this, (1), the microparticle eliminating ability of membrane once used, is not known and most of the integrity tests are a destructive test; (2) it is almost impossible to completely eliminate the substance remaining within the membrane after its use and the elimination cannot be quantified; and (3) process validation including regeneration step of membrane is difficult.

As to the causes (2) and (3) above, if there is established the microparticle eliminating performance by a method implemented by a membrane maker, i.e. if the cause (1) has been solved, both the causes above will be readily solved by employing an appropriate membrane treatment system.

For instance, assuming the microparticle eliminating performance remains over a target value even after 4 times repetition of regeneration treatment, the membrane system as a whole will be able to obtain the same performance with good reproducibility, with a membrane treatment system of five units of treatment, i.e. the un-used membrane, one-time regenerated membrane, two-times, three-times and four-times regenerated membranes. The worst case required in the process validation will correspond to a membrane treatment process comprised of membranes after four-times of regeneration.

Patent Document 1: Japanese Published Patent No. S62-044017
Patent Document 2: Japanese Published Patent No. H2-46608
Patent Document 3: Japanese Patent Application "Kokai" No. 2005-40756
Patent Document 4: Japanese Patent Application "Kokai" No. H7-132215
Non-Patent Document 1: "Investigations about Separating Membranes" Vol. 1, Vol. 2, Vol. 3: Osaka Chemical Marketing Center (1980, 1981, 1982)
Non-Patent Document 2: "Physical Properties of Polymers (3)" compiled by The Society of Polymer Science Japan, Kyoritsu Shutsugan, p. 50, 1995
Non-Patent Document 3: S, Manabe et al. "Polymer J." Vol. 18 (No. 17), pp 1-14 (1986)

DISCLOSURE OF THE INVENTION

Objects to be Achieved by the Invention

The first object of the present invention relates to a pore diffusion type flat membrane separation apparatus, the object being to provide inexpensively the pore diffusion type flat membrane separation apparatus which uses, as the solid-liquid separating method, not filtration requiring application of transmembrane pressure difference, but pore diffusion, thereby to relieve pore clogging of the membrane and which also allows reuse of the membrane.

The second object of the present invention relates to a flat membrane concentration apparatus capable of solving concentration reduction in the target substance whish is a shortcoming of the pore diffusion technique, the object being to provide a flat membrane concentration apparatus which provides a function of concentrating a particular component in a solution and which is light-weight and of a simple construction, thus being readily handled.

More particularly, the object is to provide a concentrating apparatus whose membrane housing is reusable, having the features of (a) increase of collection ratio of concentrated component, (b) minimization of osmotic pressure during concentration, (c) weight reduction, (d) capability of an intermediate molecular weight component having a molecular weight of 1000 or more, (e) ability of continuous concentration, and (f) sanitary property.

The third object of the invention relates to a regenerated cellulose porous membrane, the object being to design a porous membrane tanking into consideration, not only elimination of microorganisms, but also permeability of useful substance and readiness of use, from the viewpoint of practical application of the pore diffusion technique, and to provide a method of manufacturing such porous membrane.

The fourth object of the present invention relates to a method of inspecting a flat membrane, the object being to provide a method of inspecting a flat membrane using a non-destructive and direct membrane integrity inspection method so as to allow reuse of the membrane as a microparticle eliminating membrane.

Means to Achieve the Objects

[1] Pore Diffusion Flat Membrane separation Apparatus

In the context of the present invention, the language "pore diffusion" refers to a movement of substance through pores of the membrane, utilizing a concentration difference, which has a function of effecting separation based on degree of activity of Brownian motion of the substance molecules. With the conventional diffusion dialysis, the separation is effected based on affinity between the membrane and the substance and thermodynamics of the membrane material molecules (i.e. micro Brownian motion), by movement of the substance through a semipermeable membrane. With the pore diffusion technique, with increase in the affinity between the substance and the membrane material molecule, the diffusion coefficient decreases. Conversely, the coefficient increases in the case of dialysis diffusion.

Then, in view of the various situations described above, the present inventors intensively studied the construction, structure and the components of the flat membrane module and discovered that the above problem can be solved by configuring a support plate structure for supporting a flat membrane and through extensive analysis of the module construction suitable for carrying out pore diffusion.

For accomplishing the above-noted first object, according to a first characterizing feature of a pore diffusion type flat membrane separation apparatus of the invention, the apparatus comprises: a plurality of flat membranes and a plurality of flat plate-like supports arranged alternately with each other, said each flat membrane defining a plurality of pores and configured to separate a predetermined dispersed substance contained in a solution by a pore diffusion technique, said each flat plate-like support having a flow conduit on one or both faces thereof;

wherein;

a ratio between a spatial volume of said flow conduit and a membrane area of said flat membrane is set from 0.04 to 0.4 centimeters;

said flat plate-like support includes, in at least two positions in a lateral face thereof, water conduits in communication with said flow conduit, so that flow directions of said solution in said flow conduits of upper and lower flat plate-like supports across said flat membrane may be substantially same directions;

the outer side plate-like support includes said flow conduit in one face thereof, the water conduit in communication with said flow conduit being provided in the lateral face of this plate-like support;

the intermediate plate-like support includes said flow conduit in both faces thereof, the water conduits in communication with said respective flow conduit being provided in the lateral face of this flat plate-like support;

a treatment liquid subjected to the diffusion treatment is caused to flow under the flat membrane and a diffusion liquid in which the dispersed substance flows is caused to flow on and upwardly of the flat membrane; and said flat plate-like support and said flat membrane can be assembled with and disassembled from each other.

With the above-described construction, the greatest feature thereof lies in limiting the construction to the pore diffusion type. In the pore diffusion technique, substantially no pressure (transmembrane pressure difference) is applied to the membrane. Therefore, unlike the case of its application for filtration, a flat membrane module having a large effective filtering area becomes possible. In a pore diffusion module, the roles of the membrane support are making liquid flow circuit appropriate and preventing generation of pressure associated with liquid flow.

With the pore diffusion type flat membrane separation apparatus having the above construction, comprising: a plurality of flat membranes and a plurality of flat plate-like supports arranged alternately with each other, said each flat membrane defining a plurality of pores and configured to separate a predetermined dispersed substance contained in a solution by a pore diffusion technique, said each flat plate-like support having a flow conduit on one or both faces thereof; the ratio between a spatial volume of said flow conduit and a membrane area of said flat membrane is set from 0.04 to 0.4 cm; and said flat plate-like support includes, in at least two positions in a lateral face hereof, water conduits in communication with said flow conduit, so that flow directions of said solution in said flow conduits of upper and lower flat plate-like supports across said flat membrane may be substantially same directions.

In the above, the language "substantially same directions" means that the directions of respective pressure gradients required for flowing the two kinds of liquid are in agreement within range of 90 degrees.

If the ratio between the spatial volume of the flow conduit and the membrane area is less than 0.04 cm (excluding 0.04 cm per se), there is the risk of significant stagnation in the liquid flow, thus hindering efficient pore diffusion. If this ratio exceeds 0.4 cm, there will occur reduction in the contacting portion between the liquid and the membrane, thus making efficient pore diffusion difficult.

Therefore, if the ratio between these is within the range from 0.04 to 0.4 (unit of centimeter), smooth liquid flow can be maintained and pore diffusion can be carried out in an efficient manner. In these respects, there can be obtained sufficient advantages in effecting pore diffusion.

For effecting pore diffusion, by rending the flow conduits of the upper and lower supports across the membrane same directions, it becomes possible to equate the pressures associated with the liquid flow on the upper and lower sides of the membrane (to make same the directions of pressure gradients generating the flow), whereby generation of transmembrane pressure difference can be restricted.

Further, by providing the water conduits communicated with the flow conduit in two or more portions in the lateral face of the support, the liquid subjected to the diffusion treatment (referred to simply as "diffused liquid" hereinafter) and the liquid into which the diffused substance flows (referred to simply as "diffusing liquid" hereinafter) can be caused to flow at fixed speeds. During the diffusion, the diffused liquid flows under the membrane along the flow conduit, whereas the diffusing liquid flows on and upwardly of the membrane. And, if pore diffusion occurs through the membrane and the flows of the diffused liquid and the diffusing liquid take place without mixing therebetween, a constant state can be realized in the diffusion. That is to say, a constant diffusion state can be achieved.

With realization of such constant diffusion state, this makes it possible for the substance separating process utilizing pore diffusion to be a continuous process. Also, by providing the water conduit of the support in its lateral face, it becomes possible to stack a plurality of such supports. Hence, the entire apparatus can be formed compact and as the adjustment of the membrane area can be done easily, the effective membrane area can be changed freely.

Further, with the above inventive construction, the flat plate-like support and the flat membrane can be assembled with and disassembled from each other. By stacking a plurality of supports, the membrane areas can be adjusted as desired and the supports, together with the membrane modules, become reusable.

In the above, in the case of the conventional separating method relying on filtration, as a pressure is applied to the membrane, there occurs a flow as a fluid within the pores and also a shearing stress will be applied to the substance in the liquid, thus causing dynamic change of molecules and clogging within the pores. Further, as the membrane too is subjected to the pressure, there will occur compacting in the membrane per se disadvantageously. That is to say, in case the separation is effected by means of filtration, it becomes difficult to reuse both the membrane and the support. As a result, there occurs the problem of cost increase.

With the above inventive construction, the separating method by pore diffusion technique utilizes the Brownian motion which is thermal mobility of the molecules of the substance per se. Hence, the pore clogging can be relieved and there occurs no dynamic change of molecules, either. Therefore, as the membrane is not subjected to any large dynamic load, the module including the membranes and the supports can be reused, by effecting a simple regenerating treatment, such as cleaning of the membrane surface alone. Consequently, the costs of the membranes used can be reduced.

According to a second characterizing feature of a pore diffusion type flat membrane separation apparatus of the present invention, a packing formed of a polymer elastic member is provided in a peripheral portion of at least one of the upper and lower faces of the flat plate-like support.

With the above inventive construction, a packing is provided on one or both faces of the membrane support so as to allow the membrane to be fixed in gapless contact with the support and also to prevent liquid leakage for promoting pore diffusion, whereby the support and the membrane are integrated with each other to facilitate handling and assembly. Preferably, the material for the packing is a polymer elastic material having heat resistance and alkaline resistance.

According to a third characterizing feature of the pore diffusion type flat membrane separation apparatus of the present invention, said flat plate-like support is formed of a material having all of heat resistance, shock resistance, alkali resistance, acid resistance, light weight and transparency, the material being selected from the group consisting of polycarbonate, polyamide, polyacetal, polysulphone, polyether sulphone, and polyether ether sulphone.

With the above inventive construction, the membrane support has all of heat resistance, shock resistance, alkali resistance, acid resistance, light weight and transparency. Here, the term "heat resistance" means a property capable of withstanding a treatment with hot water of 100° C. or steam of 110° C. The term "alkaline resistance" means resistance against 0.1 normality sodium hydrate. The term "acid resistance" means resistance against 0.1 normality hydrochloric acid. Specifically, the membrane support will be selected from materials, of polycarbonate, polyamide, polyacetal, polysulphone, polyether sulphone, and polyether ether sulphone.

According to a fourth characterizing feature of the pore diffusion type flat membrane separation apparatus of the present invention, the apparatus further comprises a heat-resistant connecting member detachably connectable to the water conduit of the flat plate-like support, and the flat plate-like support is formed of polycarbonate.

With the above inventive construction, in order to further ensure the sanitary property of the module, a connecting member detachably connectable to the water conduit of the membrane support may be used. When the used module is to be cleaned, this connecting member will be detached to facilitate the cleaning. Preferably, the connecting member is formed of polycarbonate and has heat resistance.

[2] Flat Membrane Condensing Apparatus

For accomplishing the second object, according to a first characterizing feature of a flat membrane concentration apparatus of the present invention, the apparatus comprises at least two flat membranes and at least three flat plate-like supports, said membrane having a plurality of pores having an average pore diameter of from 1 to 3 nm and configured to separate a predetermined dispersed substance contained in a solution by membrane permeation;

said membrane being sandwiched between a pair of said supports which are formed like flat plates;

said support defines an inlet, a flow conduit and an outlet for said solution;

a pressure over the atmospheric pressure is applied to the side of the solution, as a stock solution, of the flat membrane whereas a negative pressure under the atmospheric pressure is applied to the side of the filtered liquid through the membrane, thereby generating an transmembrane pressure difference and causing pervaporation simultaneously with the filtration, so that a component in said solution is concentrated by parallel filtration which proceeds while the solution is caused to flow substantially parallel with the surface of the flat membrane.

With the above-described construction, the greatest feature thereof lies in the use of a flat membrane. Using a flat membrane allows increase in the collection ratio in the concentration. When hollow fibers are used, the transmembrane pressure difference can be increased without using any support, so that the concentration ratio can be enhanced in principle. However, as it will often happen that a component of the highest concentration ratio will remain within the inner wall portion of the hollow fiber, the collection ratio of the component will be lowered. Efficient collection of highly concentrated component on the membrane surface is essential for enhancement of collection ratio.

By configuring the construction as a flat membrane as the above inventive construction, dissolution collection of highly concentrated component on the membrane surface can be readily carried out, with using e.g. a small amount of water. Moreover, it becomes also possible to physically clean the surface of the flat membrane and collect it, by disassembling the flat membrane module into individual components.

Preferably, the thickness of the flat membrane should range from 10 to 50 μm, in view of the operability and permeation speed of water.

With the above inventive construction, there is employed a membrane having an average pore diameter from 1 nm or more to 3 nm or less. By setting the average pore diameter at 1 nm or more, it becomes possible to restrict the concentration ratios of water-soluble substances having molecular weights of 200 or less (e.g. metal salts, amino acids, acetic acid, ethyl alcohol, etc.) and membrane concentration with an transmembrane pressure difference of 1 atm or less is made possible. By setting the average pore diameter to 3 nm or less, it becomes possible to concentrate a substance having a molecular weight of 1000 or more.

Further, with the above inventive construction, to the flat membrane, a pressure over the atmospheric pressure is applied to the side of the solution as the stock solution and at the same time, a pressure under the atmospheric pressure is applied to the side of the filtered solution through the flat membrane, whereby an transmembrane pressure difference is developed. Also, for enabling concentration of the component in the solution by parallel filtration, the support plate defines a plurality of liquid outlets.

As the transmembrane pressure difference is generated by means of the combination of pressurization and depressurization, it becomes possible to significantly reduce the pressure applied to the module as a whole. Whereby, the membrane module can be formed light-weight. Further, as the filtration and the pervaporation occur simultaneously, the concentrating speed can be increased.

According to a second characterizing feature of a flat membrane concentration apparatus of the present invention, said flat membranes, said supports, said inlets and said outlets can be disassembled, cleaned and re-assembled, individually.

With the above inventive construction, the use of the flat membrane allows designing which facilitates disassembly and assembly of each one component of the flat membranes, the supports, the inlets and the outlets. By disassembling, cleaning and then reassembling the used membrane, the sanitary performance as the membrane module can be ensured.

As the supports, the inlets and the outlets can be freely disassembled individually, cleaning of the supports, inlets and outlets and the replacement of the expendable items and/or membrane can be readily effected.

Further, by collecting the used flat membranes alone to collect the concentrated components on the membrane surfaces, the collection ratio can be enhanced.

According to a third characterizing feature of the flat membrane concentration apparatus of the present invention, said support is formed of polycarbonate; said support defines, in a surface thereof a groove along the flow direction of the solution; said inlet and said outlet are present in a lateral face of said support; and a packing is affixed to a peripheral edge portion of at least one of upper and lower faces of said support.

With the above inventive construction, by using, for the support, polycarbonate having superior pressure resistance and chemical resistance among light-weight plastic materials, the weight of the apparatus as a whole is reduced, so that transport, assembly, disassembly and cleaning operations of the apparatus can be readily carried out.

In the surface of the support, there is defined a groove for controlling the flow direction of the liquid.

By setting the inlet and the outlet in the lateral face of the support, the filtering area can be readily changed.

Moreover, by affixing, in advance, a packing to a peripheral edge portion of at least one of the upper and lower faces of the support, the assembly operation of the apparatus is facilitated. Preferably, the packing is present under a close contacting condition of such a degree as to allow easy manual removal thereof.

According to a fourth characterizing feature of the flat membrane concentration apparatus of the present invention, space between the two supports disposed on the outermost sides when assembled and the flat membranes adjacent thereto is depressurized.

With the above inventive construction, while the support made of e.g. polycarbonate has the shortcoming of being less robust than one made of metal such as stainless steel, if a plurality of supports are stacked and the space between the two supports disposed on the outermost sides when assembled and the flat membranes adjacent thereto is depressurized, a force will be applied to urge the entire apparatus inwards, so that the stable state thereof can be maintained. As a result, the above shortcoming can be overcome.

According to a fifth characterizing feature of the flat membrane concentration apparatus of the present invention, the average pore diameter of the flat membrane is set to be 2 nm or less.

With the above inventive construction, by setting the average pore diameter to 2 nm or less, substance having an intermediate molecular weight such as a peptide can be effectively concentrated. Therefore, in the diffusion separation utilizing the pores of the porous membrane, functional substance contained in the diffusing liquid can be concentrated effectively.

Incidentally, in case the average pore diameter is under 1 nm, in membrane concentration of a normal aqueous solution containing a great variety of substances having molecular weights under 200, the transmembrane pressure difference needs to be increased in correspondence with increase of the concentration ratio. The increase of transmembrane pressure difference necessitates increase of pressure-resistance of the support, which leads, in turn, to increase of the weight of the module, thus making its handling difficult.

According to a sixth characterizing feature of the flat membrane concentration apparatus of the present invention, said flat membrane is formed of hydrophilic polymer material.

If the flat membrane is formed of hydrophilic polymer material as the above inventive construction, this can restrict adsorption of water-soluble substance such as protein to the flat membrane.

According to a seventh characterizing feature of the flat membrane concentration apparatus of the present invention, said hydrophilic polymer material is regenerated cellulose.

With the above inventive construction, as the regenerated cellulose has low adsorptive property to other substances (proteins, etc.) and has also high heat resistance, which allows high-pressure steam sterilization, thus making the handling easier.

[3] Regenerated Cellulose Porous Membrane

For accomplishing the third object noted above, according to a first characterizing feature of a regenerated cellulose porous membrane of the present invention, the regenerated cellulose porous membrane comprises a regenerated cellulose membrane including a multi-layered structure having an average pore diameter (2rf) ranging from 5 to 500 nm, a membrane thickness (d) ranging from 50 to 500 μm, a porosity (Pr) ranging from 0.6 to 0.9; and a development degree of intermolecular hydrogen bond of 40% or less.

The above construction is characterized in that the membrane is configured as a pore diffusion flat membrane. With use of pore diffusion technique, the transmembrane pressure difference may be zero in principle. So, the function required for the dynamic characteristics of the membrane may be of low level. Pore diffusion depends only on the membrane diffusion speed of substance, being almost entirely unrelated to the average pore diameter. With pore diffusion, no clogging of pores inside the membrane occurs. With a flat membrane module, there hardly occurs flow resistance against the flowing of liquid, so it best suits pore diffusion technique. Needless to say, the flat membrane of the present invention may be applied to filtration technique also, but the characterizing features of pore diffusion will be lost in the case of filtration technique.

With the above inventive construction, regenerated cellulose is employed as the membrane material. When a useful substance is to be separated and collected from an aqueous solution, as the regenerated cellulose has low adsorptive property to other substances (proteins, etc.) and has also high heat resistance, which allows high-pressure steam sterilization. In the case of a separating membrane designed for microparticle elimination, it is required that the eliminating mechanism for microparticle be clearly identified. To this end, the regenerated cellulose porous membrane is suitable.

Regenerated cellulose is suitable for reducing crystallization degree of a regenerated cellulose membrane obtained by saponification treatment of a cellulose ester, or of a cellulose derivative in particular. Increase in crystallization degree would result in destruction of the multi-layered structure of particles.

With the above inventive construction, the average pore diameter is set from 5 nm to 500 μm. Here, the average pore diameter was determined by the filtration speed method of water. As the conventional separating membrane is employed in the filtration technique, as a separating membrane, no membrane has been developed yet which has an average pore diameter of 10 nm or less.

There has been a need to eliminate prions from blood plasma fraction formulation, bovine serum, etc. To achieve this end, the pore diffusion technique using a flat membrane having an average pore diameter ranging from 5 to 10 nm is most promising. In the case of the conventional micro phase separation technique, with decrease in the average pore diameter, the porosity is also decreased. For this reason, even if there is developed a membrane having an average pore diameter of 10 nm or lees, if this is used as a filtering membrane, such membrane will be of little practical use due to its low filtering speed.

Only with the use of the pore diffusion method as proposed by the present invention, there has been provided the possibility of practical application of a membrane having a small pore diameter of 5 nm to 10 nm.

For instance, an average pore diameter from 9 to 10 μm will be used for prions. An average pore diameter of 20 nm will be used for removal of virus. And, an average pore diameter of 500 nm will be used for bacterial removal and removal of mycoplasma.

In the above, if the average pore diameter is under 5 nm, this will result in reduction in the filtering speed of the useful substance, such as a protein, through the membrane in an aqueous solution, so that the practical utility of the membrane as an industrial separating membrane will be lost. In some cases, an osmotic pressure will be developed, which may cause flow of water under the osmotic pressure. On the other hand, if the average pore diameter exceeds 500 nm, the filtration technique will be more advantageous than the pore diffusion technique in the respects of both the substance permeation speed of the substance and the processing liquid amount per unit membrane area.

With the above inventive construction, the membrane, under its dry condition, has a membrane thickness (d) from 50 μm or more to 500 μm or less and the membrane has a multi-layered structure.

The moving speed of a substance in membrane varies in reverse proportion to the membrane thickness. Hence, in general, the smaller the membrane thickness, the better. On the other hand, the microparticle eliminating performance of a membrane having a porous structure will be better, with increase in its thickness. If the membrane thickness becomes under 50 μm, the microparticle eliminating performance will be significantly reduced, due to the influence of pinholes present within the membrane. Whereas, if the thickness exceeds 500 μm, this results in reduction in the membrane permeation speed of the substance.

In the case of the pores diffusion technique, the requirement for the dynamic strength of the membrane is low. Therefore, there is no reason to increase the membrane thickness for the sake of increase of membrane strength. In the case of membrane separation using pore diffusion technique, when the membrane thickness is set to 500 μm or more, this will result in significant reduction in the concentration of the useful substance in the diffusing liquid.

With the above inventive construction, the porosity (Pr) is set to be 0.6 or more and to be 0.9 or less at the same time. As a characterizing feature of the pore diffusion technique, it has been found that the average pore diameter hardly contributes to the membrane permeation speed of substance, but the porosity (Pr) contributes to the same. Therefore, it is preferred that the porosity (Pr) be set from 0.7 to 0.85.

With the above inventive construction, the development degree of the intermolecular hydrogen bond is set to 40% or less. This reduction of development degree leads, in general, to decrease in the crystallization degree. This also results in decrease in the anisotrophy in the shape change during the swelling with water. If this development degree is 40% or less, there occurs no shape change at the time of submersion in water. So, this will lessen the possibility of breakage of the flat membrane when fixed to the support. Further, there will hardly occur any changes in the pore properties (average pore diameter, porosity, and membrane thickness) in the shape of the membrane in association with the high-pressure steam sterilization.

According to a second characterizing feature of the regenerated cellulose porous membrane of the present invention, the average pore diameter (2fr) is set from 8 to 100 nm, the membrane thickness (d) is set from 100 to 300 µm, and the product of the porosity (Pr) and the membrane thickness (d) is set to 50 µm or more.

If the average pore diameter is set from 8 nm to 100 nm as proposed by the above inventive construction, the membrane may be suitably used for such elimination targets as prions, viruses, etc.

Further, in view of the balance between the eliminating performance and the permeability of the useful substance, in case the microparticle as the elimination target of the membrane separation is a virus or a prion, preferably, the membrane thickness (d) ranges from 100 µm to 300 µm.

In the pores diffusion, the transmembrane pressure difference is nearly zero. So, the dynamic load to the membrane is small, hence, the porosity (Pr) may be increased to the maximum. However, with increase of the porosity (Pr), the microparticle eliminating performance will be deteriorated. This deterioration can be avoided by increasing the membrane thickness (d). If the product of the porosity (Pr) and the membrane thickness (d) is set to 50 µm or less, it is possible to obtain appropriate balance between the microparticle eliminating performance and the membrane permeation speed of the useful substance.

According to a third characterizing feature of the regenerated cellulose porous membrane of the present invention, the product of the porosity (Pr) and the membrane thickness (d) is set to range from 100 µm and 200 µm.

If the product of the porosity (Pr) and the membrane thickness (d) is set to range from 100 µm and 200 µm as proposed by the above inventive construction, it is possible to obtain even more appropriate balance between the microparticle eliminating performance and the membrane permeation speed of the useful substance.

According to a first characterizing feature of a method of manufacturing a regenerated cellulose porous membrane of the present invention, the method comprises a method of manufacturing the regenerated cellulose porous membrane as defined by the first characterizing feature of the regenerated cellulose porous membrane described above, the method comprising the steps of: forming a porous membrane by a micro-phase separation technique from a solution of cellulose ester as a cellulose derivative with addition of 1% in weight or more of a metal salt thereto; and subsequently subjecting the resultant membrane to a saponification treatment with an alkaline aqueous solution having a pH value ranging from 11 to 13 at a temperature of 50° C. or lower.

With the above inventive construction, the pore diffusion regenerated cellulose porous membrane is manufactured by: (1) the membrane forming technique by the micro-phase separation process of a cellulose derivative; and (2) a method of rendering the cellulose derivative into a regenerated cellulose by a saponification reaction. In particular, the membrane manufacture is made possible by causing the micro-phase separation solution to contain 1% in weight or more of a metal salt and selecting a specified saponification condition.

As the cellulose derivative, a cellulose ester, especially, a cellulose acetate, is preferred for the ready availability and for providing the possibility of selecting a non-aqueous solvent as a solvent for causing the micro-phase separation. The use of a non-aqueous solvent enables the micro-phase separation to take place in a short period of time and also allows use of micro-phase separation by the dry method.

If the micro-phase separation can take place in a short period of time, it becomes readily possible to manufacture a multi-layered membrane having a large membrane thickness. In the case of cellulose acetate, a great variety of effective solvents are available and an organic solvent not containing any heavy metal can be readily selected as the solvent. In such case, acetone is particularly preferred.

It has been discovered that in case the cellulose derivate is formed into a regenerated cellulose solid through the saponification reaction, this lowers the development degree of intermolecular hydrogen bond. And, with this reduction in the development degree, the heat resistance is reduced, but, such reduction in thermal resistance is of a temperature (200° C. or higher) which is not problematic as the pore diffusion separating membrane.

Further, in the case of the saponification reaction of cellulose acetate, the directions of the intermolecular hydrogen bonds within the membrane after the micro-phase separation are random, so that there occurs no anisotrophy in the swelling relative to water. Further, there occurs no anisotrophy in deformation due to high-pressure, high-temperature hot water treatment. With the saponification reaction, the porosity will increase generally and at the same time the average pore diameter will decrease.

However, in case the membrane prior to the saponification reaction has an average pore diameter of 9 nm or less, the saponification reaction results in enlargement of the average pore diameter, conversely. Then, by utilizing this property, a regenerated cellulose membrane having an average pore diameter of 10 nm or less can be manufactured.

If the flow casting solution is caused to contain 1 percent in weight or more of metal salt, in addition to a good solvent, a poor solvent, and a surface tension regulating agent, removal of the membrane from the support after the micro-phase separation and control of the pore properties of the front and back faces of the membrane become easy.

As the metal salt, a hydrochloride salt or acetate salt of an alkaline earth metal is suitable. Calcium chloride is particularly suitable. In adding the metal salt, preferably, by preparing this as a chemical substance bonded with crystalline water, a predetermined amount of water is caused to be contained therein. The addition amount will be determined, based on the total weight including this crystalline water.

In effecting the saponification treatment to the membrane after the micro-phase separation, this needs to be effected under a condition where significant reduction in the molecular weight of the cellulose derivative will not result therefrom. More particularly, this will be effected under mild conditions with an alkaline aqueous solution having a pH from 11 to 13 at a temperature of 50° C. or lower.

The alkaline aqueous solution will be prepared with a caustic soda or caustic potash. Even under such mild conditions as above, 24 hours of less reaction time will be sufficient. And, the membrane after the micro-phase separation may be either dry or wet. The probable reason why the saponification reaction proceeds speedily is that the flat membrane after the micro-phase separation is porous and its solid portion is under non-crystalline state.

According to a second characterizing feature of a method of manufacturing a regenerated cellulose porous membrane of the present invention, the method comprises a method of manufacturing the regenerated cellulose porous membrane as defined by the second characterizing feature of the regenerated cellulose porous membrane described above, the method comprises the steps of: forming a porous membrane by a micro-phase separation technique from a solution of cellulose acetate as a cellulose derivative with addition of 1% in weight or more of a metal salt thereto; and subsequently subjecting the resultant membrane to a saponification treatment with an alkaline aqueous solution having a pH value ranging from 11 to 13 at a temperature of 50° C. or lower.

With the above inventive construction, as the cellulose acetate is employed as the cellulose ester, in addition to the above-described function/effect of the first characterizing feature of the method of manufacturing a regenerated cellulose porous membrane, the method further provides greater readiness of availability and superior safety.

According to a third characterizing feature of a method of manufacturing a regenerated cellulose porous membrane of the present invention, the method comprises a method of manufacturing the regenerated cellulose porous membrane as defined by the third characterizing feature of the regenerated cellulose porous membrane described above, the method comprises the steps of: forming a porous membrane by a micro-phase separation through evaporation of a good solvent of a cellulose ester, from a solution of cellulose ester as a cellulose derivative with addition of 1% in weight or more of a metal salt thereto; and subsequently subjecting the resultant membrane to a saponification treatment with an alkaline aqueous solution having a pH value ranging from 11 to 13 at a temperature of 50° C. or lower.

With the above inventive construction, as the micro-phase separation is caused by evaporation of good solvent of the cellulose ester, in addition to the above-described function/effect of the first characterizing feature of the method of manufacturing a regenerated cellulose porous membrane, the method further provides effective occurrence of the micro-phase separation through the evaporation process.

[4] Method of Non-Destructive Inspection of Flat Membrane

For accomplishing the above-noted fourth object, according to a first characterizing feature of a method of non-destructive inspection of a flat membrane according to the present invention, in order to allow reuse of a flat membrane having a plurality of pores and configured for separating a particular dispersed substance contained in a solution through pore diffusion technique, the method comprises an integrity test step for confirming that particle eliminating ability of the flat membrane has not been reduced, by means of a direct method utilizing microparticles other than noble metals.

With the above inventive construction, the inspection method of microparticle eliminating ability and integrity test method of membrane become identical to each other. Normally, the inspection method of microparticle eliminating performance is conducted by the maker of the membrane, whereas the integrity test is conducted by the user of the membrane, so these methods are different. And, as the membrane maker has recommended one-time use of membrane, the integrity test is done as a destructive test. Moreover, the inspection sensitivity has remained insufficient as a method of inspecting eliminating performance and substantially no technical progress has occurred so far. Now that these methods have been rendered identical to each other, an actually determined value obtained from the integrity test directly represents a value of eliminating performance.

With the above inventive construction, as the integrity test method, a non-destructive direct method is employed. As the method is a non-destructive method, the testing result is equivalent to confirmation of the used membrane having a microorganism eliminating ability which would be obtained by an integrity test. That is to say, the integrity test plays a role as the performance test of the membrane to be reused.

Further, as the method is a direct method, it is possible to minimize influence to interfacial change of the membrane. It is further preferred that a regeneration treatment be effected on the membrane prior to effecting of the integrity test.

In either the integrity test or the eliminating performance test, if the pore diffusion technique is employed in the course of membrane treatment with colloid dispersion liquid. Remaining of colloid particles within the membrane as the result of test will not occur. Hence, regeneration of membrane after the test can be readily carried out. If the pore diffusion technique is employed in separation refining process using the membrane after the performance test, substantially no substance will remain within the pores of the membranes, so that the regeneration use of the membrane will be further facilitated.

With the above inventive construction, the integrity test is conducted on the membrane after its use in the membrane separation technique using flat membrane. The reason why the integrity test is required in the membrane separation technique using a flat member is need to confirm the microparticle eliminating performance. In this case, as the membrane separation technique, the membrane permeation technique and the pore diffusion technique are employed. The former case comprises filtration with flow of solution (filtration referred to as parallel filtration, tangential flow filtration, cross-flow filtration), in which the transmembrane pressure difference applied is smaller than that applied in the dead-end filtration. That is, in the membrane separation technique using a flat membrane for micro particle elimination, the membrane separation is effected under a condition of minimizing the effect of concentration polarization. For this reason, it is not absolutely needed to effect a dissolution elimination treatment on the membrane, prior to conducting the integrity test thereon. As long as it is confirmed in advance that components adsorbed to the membrane and the microparticles used in the integrity test will not adsorb to each other in the aqueous solution, the dissolution elimination of the membrane prior to integrity test is not absolutely needed.

If the membrane separation technique using a flat member comprises the pore diffusion technique, then, in most cases, the dissolution elimination of the membrane prior to the integrity test is not needed. For, clogging of pores in the membrane with particles or the like will hardly occur, in the case of the pore diffusion technique. Therefore, the pore diffusion technique is preferably used as the membrane separation technique. However, there can sometimes occur a situation where a particular component is adsorbed to and accumulated on the membrane surface. In such situation, as there exists the possibility of interaction such as adsorption between the microparticles used in the integrity test and the accumulated substance, the dissolution elimination of the membrane prior to integrity test becomes needed.

In such case requiring the dissolution elimination of the membrane prior to integrity test, in general, the dissolution elimination conducted in the following sequence will be advantageous also for reuse of the membrane. Namely, (1) sterilization of membrane: membrane is submerged in aqueous solution of perchloric acid, or hydrogen peroxide water is charged in the module; (2) 0.1 normality sodium hydrate aqueous solution with a surfactant is charged in the module;

(3) reverse-washing with purified water such as distilled water; and (4) submerged in 0.1 normality sodium hydrate aqueous solution; (5) water-washing the inside and outside of the module; (6) submerged in 0.1 normality hydrochloric acid; and (7) water-washing to render the pH to 7 substantially.

Conventionally, the integrity test using a flat membrane was an indirect method. With the indirect method using a flat membrane, the transmembrane pressure difference applied is normally lower than 1 atm. Therefore, the integrity test would employ solvent other than water, and the solvent would remain within the membrane after the test, thus resulting in a change in the physiochemical characteristics of the membrane. In this regard, the integrity test is a destructive test. As long as the particle eliminating membrane is for one-time use as conventionally, there is no need for direct and non-destructive type integrity test.

Only when the object of reusing the membrane is provided in the development of membrane separation technique, there arises the necessity for the direct and non-destructive integrity test for a flat membrane, thus arriving at the present invention.

If the test is to be a non-destructive integrity test, it is required that the particles employed in this test be not chemically or physically stable. More particularly, it is required that the particles be microparticles other than noble metals. For this reason, the gold colloid particles conventionally employed in the direction are unsuitable.

In the non-destructive direct method as the integrity test, with use of microparticles other than noble metals, microparticles adhered to the membrane after the integrity test can be removed easily.

According to a second characterizing feature of the method of non-destructive inspection of a flat membrane of the present invention, the method further comprises a dissolution eliminating step for dissolving and eliminating the microparticles, after said integrity test step.

With the above inventive construction, in the membrane used in the integrity test, substances other than those constituting the membrane will remain within the membrane through adsorption or clogging. In particular, if the filtration technique is employed as the membrane treating method, this will result in increase of the substance remaining within the membrane. Then, by dissolving these remaining substance by the dissolution eliminating process, the membrane is regenerated.

The microparticle eliminating performance is confirmed by the integrity test on this membrane. Although contribution of large pores to substance transport can be elucidated through this integrity test, there is the possibility that the average performance of the entire pores has not been regenerated yet. Then, in order to confirm the reusability more reliably, preferably, on the regenerated membrane, determination is made for water transmission speed under a predetermined transmembrane pressure to confirm the speed remains within a predetermined range.

In one example of dissolving method, the membrane after completion of the integrity test is subjected to: (A) submerging in a dissolving eliminating solution; (B) reverse-washing with a cleaning liquid; and (C) charging the dissolving eliminating solution in the module and eliminating this solution after a predetermined storage period.

According to a third characterizing feature of the method of non-destructive inspection of the flat membrane of the present invention, the dissolving eliminating agent employed at the dissolving eliminating step has characteristics of dissolving the microparticles used at the integrity test, without dissolving or swelling the material forming the flat membrane through a chemical reaction therewith.

With the above inventive construction, the dissolving eliminating agent employed at the dissolving eliminating step does not chemically react with the material constituting the flat member to cause its dissolution or swelling. Hence, the dissolving eliminating step can be carried out in a stable manner.

According to a fourth characterizing feature of the method of non-destructive inspection of the flat membrane of the present invention, said microparticles comprise ferric hydroxide colloid particles.

As the microparticles employed in the direct integrity test, amorphous low molecular colloid particles are suitable. Being amorphous, the dissolving speed in the dissolving eliminating liquid is high.

If the microparticles comprise ferric hydroxide colloid particles as proposed in the above inventive construction, there are obtained readiness of adjustment and stability of colloid particles as well as readiness of colloid particle concentration determination.

Incidentally, as to the concentration of the ferric hydroxide colloid particles, ferric hydroxide will be ionized with hydrochloric acid or the like and the determination is made by the spectroscopy.

With the ferric hydroxide colloid particles, these particles can be readily dissolved and eliminated with using an acid after the integrity test. If an aqueous solution containing ferric hydroxide colloid particles dispersed therein is added with a hydrophilic polymer additive and a cation surfactant or a non-ionic surfactant, this addition will increase the stability of the colloid particles during the integrity test.

According to a fifth characterizing feature of the method of non-destructive inspection of the flat membrane of the present invention, said material forming the flat membrane comprises hydrophilic polymer and said dissolving eliminating agent comprises hydrochloric acid.

Prior to conducting the integrity test, a regenerating treatment of the membrane is conducted, when needed. For effective prevention of adsorption of the dissolved or dispersed particles in the aqueous solution during the membrane treatment, hydrophilic polymer is suitable as the material for forming the microparticle eliminating membrane.

In dissolving and eliminating the ferric hydroxide colloid particles after the test, if an acid treatment is effected immediately after the test, the microparticles can be dissolved easily. As this acid, hydrochloric acid is preferred, for its easy availability and easy handing, etc.

As to the concentration of hydrochloric acid, the normality from 0.1 to 1 is preferred since its influence to the polymer membrane material is negligible in many cases. For complete implementation of dissolving elimination of microparticles using the dissolving eliminating agent, the dissolving eliminating agent will be mixed in advance in the aqueous solution containing the microparticles and there is obtained relationship between the treatment time and the ionization ratio of the microparticle component and then, there will be set a treatment period of twice or more longer than the period required for complete ionization and the treatment temperature will be set to be 10° C. higher than the temperature at the time of the integrity test. Then, after the dissolving elimination, the dissolving eliminating agent will be eliminated completely by water wash.

According to a six characterizing feature of the method of non-destructive inspection of the flat membrane of the present invention, the hydrophilic polymer comprises regenerated cellulose.

With the above inventive construction, for membrane treatment of aqueous solution containing protein in particular, regenerated cellulose is most suitable as the material polymer. A typical method of regeneration of regenerated cellulose membrane comprises submerging the membrane in a solution comprised of from 0.01 to 0.1 weight percent of non-ionic surfactant dissolved in from 0.1 to 0.2 normality caustic soda solution, under predetermined conditions. The purpose of the regeneration treatment prior to the integrity test is to prevent change of dispersion condition of colloid particles for the integrity test due to components adsorbed to or clogged within the used membrane, the purpose being not to regenerate the membrane to its original state before use.

BEST MODE OF EMBODYING THE INVENTION

[1] Pore Diffusion Type Flat Membrane Separation Apparatus

Next, there will be described a pore diffusion type flat membrane apparatus configured to effect solid-liquid separation through utilization of pore diffusion mechanism of a membrane.

As shown in FIGS. 1-3, the pore diffusion type flat membrane apparatus X of the invention comprises: a plurality of flat membranes 7 and a plurality of flat plate-like supports 1 arranged alternately with each other. Each flat membrane 7 defines a plurality of pores and configured to separate a predetermined dispersed substance contained in a solution by a pore diffusion technique. Each flat plate-like support 1 has a flow conduit 2 on one or both faces thereof.

A ratio between a spatial volume of the flow conduit 2 and a membrane area of the flat membrane 7 is set from 0.04 to 0.4 cm.

The flat plate-like support 1 includes, in at least two positions in a lateral face hereof water conduits 3 in communication with the flow conduit 2, so that flow directions of said solution in the flow conduits 1 of upper and lower flat plate-like supports across the flat membrane 7 may be substantially same directions.

FIG. 1 shows the pore diffusion flat membrane separation apparatus X assembled with using the three flat plate-like supports 1 and two flat membranes 7. FIG. 2 is a schematic plan view showing the flat plate-like support 1. The flat plate-like supports 1 employed in the present invention support the flat membrane 7 by vertically sandwiching it.

As to the shape thereof since the diffusion technique is employed as the solid-liquid separation technique and the membrane employed comprises a membrane like a flat plate, the support 1 is configured like a flat plate. Further, in one or both faces of the flat plate-like support 1, there are provided the flow conduits 2 for allowing smooth flow of treated liquid.

The flow conduit 2 is configured such that the treated liquid as the solution containing a dispersed substance therein and subjected to a diffusion treatment at a predetermined rate flow from an inlet 3a to an outlet 3b of a water conduit 3. The flow conduit 2 is formed concave in the surface of the fat plate-like support 1 and formed to extend with inflections and in a meandering matter from the inlet 3a to the outlet 3b of the water conduit 3. This arrangement allows the entire flat membrane 7 to come into contact with the treated liquid, so that the pore diffusion efficiency is improved. Further, as the flow conduit 2 is provided in the support 1, it is possible to prevent the entire flat membrane 7 from coming into adhering contact with the support 1.

The depth of the flow conduit 2 may vary as long as it allows efficient pore diffusion. However, the shallower the conduit, the better, so as to maximize the area of contact of the treated liquid with the flat membrane 7. Preferably, the depth ranges from 0.05 cm to 0.3 cm, approximately. If the depth exceeds 0.3 cm, the flat plate-like support 1 needs to be formed thick correspondingly, whereby its handling becomes difficult. Conversely, if the depth is under 0.05 cm, then, the contact area of the treated liquid with the flat membrane 7 is reduced, so that the pore diffusion will not proceed efficiently, and the there will occur stagnation of the liquid flow.

At two or more positions in a lateral face of the flat plate-like support 1, the water conduits 3 are provided in communication with the flow conduit 2, so as to act as the entrance and exit for the treated liquid. In this, arrangement is provided such that the flow directions of the liquids on the upper and lower sides across the flat membrane 7 are same directions, so as to effect the diffusion without application of any pressure to the flat membrane 7.

With the pore diffusion flat membrane separation apparatus X of the invention, as the plurality of supports are stacked along the vertical direction, the membrane area can be adjusted as desired.

As to the fixing of the flat plate-like supports 1, preferably, threaded holes 4 are provided along the perimeter of the flat plate-like support 1 and the support is fixed by means of screws 8 and nuts 9 as fasteners. The number and the spacing of the threaded holes 4 may be adjusted in accordance with the size and the area of the module. As the fasteners 8, 9, material having good corrosion-resistance, such as stainless steel, may be employed. Further, as the flat membrane 7 and the flat plate-like support 1 are not bonded with each other with adhesive or the like, these components can be assembled with and disassembled from each other. Therefore, even if a portion of the flat membrane 7 and/or the flat plate-like supports 1 is damaged, that damaged portion alone can be replaced. Further, the above arrangement facilitates regeneration of the membrane, so that the costs of the pore diffusion flat membrane separation apparatus X can be restricted.

At a peripheral edge portion of at least one of the upper and lower faces of the flat plate-like support 1, there is provided a packing 5 formed of polymer elastic material.

As to the material forming the packing 5, any material will do as long as it can be applied in such a manner as to surround the peripheral edge of the flat plate-like support 1 and allows fixing of the flat membrane 7 with this packing 5 and it also can prevent leak of the treatment liquid from the lateral faces of the pore diffusion flat membrane separation apparatus X and allows efficient pore diffusion.

Preferably, the material is a polymer elastic material having both heat resistance and chemical resistance. For instance, a silicone rubber or the like can be employed. And, also preferably, the degree of adhesion between the packing 5 and the flat plate-like support 1 is such that these are adhered to each other when they are pressurized by the fasteners 8, 9 and which are in weak contact with each other when the flat membrane 7 and the flat plate-like supports 1 are separated from each other and the packing can be removed manually, if necessary.

The material forming the flat plate-like support 1 may be selected from the group consisting of plastic materials such as polycarbonate, polyamide, polyacetal, polysulphone, polyether sulphone, and polyether ether sulphone ketone, polyethylene or an inorganic material such as stainless steel, ceramics, etc. In view of e.g. repeated use thereof, it is preferred that the material have all of heat resistance, shock resistance, alkaline resistance, acid resistance, light weight and a certain degree of transparency. On example of plastic material having such properties is engineering plastics. For instance, polycarbonate is employed advantageously.

There is provided a connecting member 6 to be connected with an external conduit, the connecting member 6 being detachably connectable to the water conduit 3 of the flat plate-like support 1. This connecting member 6 may be formed of any material. For instance, a plastic material such as polyethylene or "Teflon" (registered trademark) may be employed. However, in order to allow in-line sterilization for example, a material having heat resistance and steam resistance, e.g. crystalline polymer of polyethylene polypropylene is preferred.

The flat membrane 7 of the invention does not require any special adhesive bonding with the flat plate-like supports 1. Further, as the flat membrane 7 per se does not require any special working, any membrane as long as it is in the form of a flat membrane, may be employed. However, as the pore diffusion technique is employed as the separating method, it is preferred that the membrane be a porous membrane having an average pore diameter ranging from about 2 nm to about 2 µm and a porosity from 40% to 90%.

EXAMPLE 1

A flat plate-like support 1 formed of a polycarbonate plate (referred to as "support" hereinafter) is formed like a flat plate having a plate thickness of about 0.6 cm, a length of 40 cm and a width of 50 cm. And, in one or both faces thereof, there is formed a concave flow conduit 2 having a width of about 1.5 cm and a depth of 0.1 cm, the conduit 2 being in communication with a water conduit 3 from its inlet 3a to its outlet 3b.

The water conduit 3 functions as entrance/exit for the treatment liquid. In a lateral face of the support 1, there are formed holes having a diameter of about 0.4 cm from the leading end to the terminal end of the flow conduit 2 to be continuous therewith. This ensures flow of the treated liquid along a predetermined direction.

The thread holes 4 are formed with an inter-hole spacing of 5 cm. And, these are formed directly in the support 1. Then, screws 8 are inserted into them to fix the support 1. The screws 8 need not provide the fixation with using all of the screw holes 4. The number and the positions thereof may be adjusted as needed.

Referring to the packing 5, a silicone type adhesive was applied and adhered in a width of about 0.7 cm between the flow conduit 2 and the screw holes 4 of the support 1. After polymerization solidification thereof there was formed a packing 5 having a thickness of 0.05 cm. With this packing 5, the flat membrane 7 may be affixed with greater sealing of the inside of the pore diffusion flat membrane separation apparatus X.

FIG. 1 shows a pore diffusion flat membrane separation apparatus X assembled with using three supports 1 and two flat membranes 7. The outer support 1a includes the flow conduit 2 and the packing 5 in one face thereof and water conduits 3 in a lateral face. The intermediate support 1b includes the flow conduits 2 and the packings 5 in both faces thereof and includes the water conduits 3 in a lateral face thereof.

The flat membrane 7 is a porous flat membrane formed of regenerated cellulose and having an average pore diameter of 30 nm, a porosity of 65% and a membrane thickness of 170 microns. This flat membrane 7 is a single sheet of membrane having a membrane area (about 2000 cm²) equal to or greater than the packing 5 formed on the support 1. And, this flat membrane 7 is sandwiched between supports 1 and then fixed by screws 8. In this, the supports 1 are oriented such that the directions of the flow conduits 2 thereof may be a same direction. A connecting member 6 formed of polyethylene was inserted into the water conduit 3, whereby the pore diffusion type flat membrane apparatus X was manufactured as an apparatus capable of pore diffusion with a pump operably coupled therewith.

As the treated liquid, there was employed a solution of ferric hydroxide colloids having an average pore diameter of 27 nm. In operation of the pore diffusion type flat membrane separation apparatus X of the present invention, the treated liquid to be subjected to a diffusion treatment at a predetermined rate was caused to flow under the flat membrane 7 from the inlet-side water conduits 3a along the respective flow conduits 2 and collected on the outside of the apparatus past the outlet-side water conduits 3b. Further, the diffusing liquid in which the diffused substance was to be mixed was caused to flow on the flat membranes 7 from the inlet-side water conduits 3a along the flow conduits 2 and then collected on the outside of the apparatus past the outlet-side water conduits 3b.

In the course of the above, there occurs pore diffusion through the flat membranes 7, so that the dispersed substance contained in the treated liquid flows into the diffusing liquid and as there occurs the flow of a predetermined rate without mixing of the diffused liquid and the diffusing liquid, there can be realized diffusion under a constant condition.

Further, with the packing 5, the degree of sealing of the apparatus is enhanced, so that the fixation of the flat membranes 7 can be sufficient. Moreover, as the flat membranes 7 and the flat plate-like supports 1 are provided independently of each other, it was readily possible to reassemble the pore diffusion flat membrane separation apparatus X after this was disassembled and also possible to increase the membrane area by increasing the number of the flat membranes 7.

Incidentally, for the treated liquid, there are established following Mathematical Formulae 3, 4, with $V_A$: a treatment liquid amount introduced from the inlet-side water conduits $3a$, $C_{AIN}$: concentration thereof; $C_{AOUT}$: concentration of the liquid discharged from the outlet-side water conduits $3b$, and for the diffusing liquid, $V_B$: a treatment liquid amount introduced from the inlet-side water conduits $3a$, $C_{BIN}$: concentration thereof, $C_{BOUT}$: concentration of the liquid discharged from the outlet-side water conduits $3b$.

where, D: intra-pore diffusion constant, S: membrane area, d: membrane thickness.

$$C_{Aout} = \left(\frac{v_B(C_{Ain} - C_{Bin})}{v_A + v_B}\right)\exp\left(-\frac{DS(v_A + v_B)}{v_A v_B d}\right) + \frac{v_A C_{Ain} + v_B C_{Bin}}{v_A + v_B}$$

[Mathematical Formula 3]

$$C_{Bout} = \left(\frac{v_A(C_{Bin} - C_{Ain})}{v_A + v_B}\right)\exp\left(-\frac{DS(v_A + v_B)}{v_A v_B d}\right) + \frac{v_A C_{Ain} + v_B C_{Bin}}{v_A + v_B}$$

[Mathematical Formula 4]

For instance, if the operating condition is: $V_A = V_B = V$, $C_{BIN} = 0$, there are established the following Mathematical Formulae 5 and 6, where $C_{AOUT}$: concentration change in treated liquid, $C_{BOUT}$: concentration change in diffusing liquid.

$$C_{Aout} = \frac{C_{Ain}}{2}\left(1 + \exp\left(-\frac{2DS}{vd}\right)\right)$$

[Mathematical Formula 5]

$$C_{Bout} = \frac{C_{Ain}}{2}\left(1 - \exp\left(-\frac{2DS}{vd}\right)\right) \qquad \text{[Mathematical Formula 6]}$$

FIG. 11 shows a graph illustrating relationship between residence time (h) and concentration (g/dL) between treated liquid and diffusing liquid. Incidentally, the residence time can be obtained by dividing the volume of flow conduit by the flow amount.

The collection ratio (%) can be obtained by dividing the decrease amount of treated liquid concentration by the entrance concentration of treated liquid. FIG. 12 shows a graph illustrating relationship between the collection ratio (%) and the flow amount (L/h·m²).

The above-described pore diffusion type flat membrane separation apparatus X permits reuse of the flat membrane 7 utilizing the diffusion phenomenon of useful substance via pores included in the porous membrane, whereby the pore diffusion type flat membrane separation apparatus X can be provided economically.

[2] Flat Membrane Concentration Apparatus

Next, there will be explained a flat membrane concentration apparatus for concentrating, with a high collection ratio, a useful substance from a solution, through parallel filtration using a flat membrane, such as an aqueous solution containing a biologically active agent, an extraction process liquid from industrial waste.

This flat membrane concentration apparatus includes a flat membrane having a plurality of pores having an average pore diameter ranging from 1 nm to 3 nm, for separating a predetermined dispersed substance from a solution, through filtration. As shown in FIGS. 4 through 6, the flat membrane concentration apparatus Y comprises flat membranes 7 sandwiched between flat plate-like supports 1, and includes at least two flat membranes 7 and at least three sheets of supports 1, the support 1 defining a solution inlet 3a, flow conduit 2 and outlet 3b.

In operation of the flat membrane concentration apparatus Y, the side of solution, as stock solution, of the fat membrane 7 is increased over the atmospheric pressure, whereas the filtered liquid side of the liquid past the flat membrane 7 is decreased below the atmospheric pressure, thereby generating an transmembrane pressure difference, which causes the solution to flow substantially parallel with the surface of the flat membrane 7 and filtered thereby at the same time, this parallel filtration separating a component from the solution.

A cellophane membrane wet-formed by a known method was treated at its free end for one hour in hot water at 95° C. After the treatment, water was removed therefrom and the resultant membrane was dry heat-treated in nitrogen gas pressure at 180° C., whereby a regenerated cellulose having an average pore diameter of 1.5 nm and a porosity of 20% was manufactured. Regenerated cellulose is one example of hydrophilic polymer.

The porosity is calculated from an actually determined value of an apparent density of membrane, with the density of regenerated cellulose being 1.54 g/ml. The average pore diameter is calculated by determining a filtration speed of purified water under a predetermined transmembrane pressure difference (method called "filtration speed determining method").

A support 1 formed of polycarbonate (thickness: 6 mm, length 45 cm×width: 55 cm) defines a groove having a depth of about 1 mm as a flow conduit 2. In the periphery of the support 1, there is formed a packing 5 by applying and adhering a silicone type filling agent. The packing 5 has a thickness which ranges from 0.5 to 1 mm for example. For the flow conduit 2, at two positions in a later face of the support 1, there are provided inlets 3a and outlets 3b (inner diameter: 3 mm) for communication with a flow conduit outside the support 2, and into the inlets 3a and outlets 3b, there are inserted connecting members which are attachable to and detachable therefrom.

With the regenerated cellulose membranes manufactured by the above-described method being sandwiched by supports 1, two regenerated cellulose membranes and three supports 1 are assembled with each other and the supports 1 being bolt-fastened and fixed. Then, connecting members are inserted into the inlets 3a and the outlets 3b to be connected to external flow conduits. The treatment liquid is introduced under a pressurized condition into the intermediate support 1b so that the spaces within the two outer supports 1a are at a pressure of −0.2 atm with an transmembrane pressure difference of 0.3 atm. For instance, in order to concentrate 3 L of un-treated liquid into 300 mL, about 12 hours of filtration is needed, in the case of an effective filtering area of 1 m².

EXAMPLE 2

FIG. 4 is a view schematically showing a flat membrane concentration apparatus Y. The flat membrane concentration apparatus Y comprises an alternatively superposed assembly of supports 1 and flat membranes 7. The atmospheric pressure is applied to the outer support 1a, thus increasing the close contact between the supports and increasing the packing effect.

FIG. 5 is a schematic vertical section of the flat membrane concentration apparatus Y. The dot line shown represents omission of a plurality of supports and flat members bound between, from the illustration. In this, a space 10 between the outer disposed support 1a and the flat membrane 7 is under a depressurized condition whereas a space 11 is under a pressurized condition. The support on the pressurized side too defines a flow conduit, which flow conduit facilitates collection of concentrated liquid and allows reverse washing, if necessary.

As to the support 1b and flat member 7 disposed intermediate in FIG. 5, the upper space of the flat membrane 7 is pressurized whereas the lower space thereof is depressurized. In order to facilitate distinction between the pressurized side and the depressurized side, the connecting members may be inserted with offset from each other in advance.

When treated liquid is introduced into the space under the pressurized condition, filtration takes place due to the transmembrane pressure difference relative to the space under the depressurized condition, so that the treated liquid permeated through the flat membrane 7 will flow to the space under the depressurization.

In order to effectively utilize the membrane area, air present in the pressurized space should be eliminated. To this end, it is necessary to erect the flat membrane concentration apparatus Y perpendicularly or dispose it with a slope, so as to facilitate outflow of the air to the inlets 3a, outlets 3b. In order to increase the concentration ratio of the treated liquid, the flow speed of the solution should be lowered or the filtration should be carried out in repetition. In order to avoid reduction in the collection ratio, it is preferred that the concentration ratio be 10 times or less.

FIG. 6 is a plain view of the support 1. At a peripheral edge portion of at least one of the upper and lower faces of the support 1, there is formed a packing 5. And, over the entire face where the treated liquid flows, there is formed a flow conduit 2 along the flow direction of the treated liquid. These are formed in both faces of the support, whereas these are provided only in one face in the case of the support 1a which is disposed most outwards. The material forming the support 1 is polycarbonate, which has good heat-resistance and shock-resistance.

In the case of long-term storage in a module state, storage with keeping an alkaline aqueous solution of pH>9 should be avoided since such storage can cause cracking in the support 1. For this reason, 50% ethanol aqueous solution is advantageously used, instead of the alkaline aqueous solution.

As the flow conduit 2 is provided in the support 1, it is possible to prevent the whole flat member 7 from coming into gapless contact with the support 1, thus allowing the treated liquid to flow smoothly along and over the entire flat membrane 7. The shape of the groove of the flow conduit 2 should be designed, taking into consideration, in addition to the function above, the convenience of collection of concentrated liquid and avoidance of gapless contact of the flat membrane 7 with the support. Preferably, the depth of the groove ranges from 1 to 2 mm and the spacing between the grooves should be 2 cm or less.

By rendering the space 10 in FIG. 5 to the depressurized condition, the outer support 1 will be formed concave toward the inside of the flat membrane concentration apparatus Y, thus enhancing the packing effect to prevent liquid leakage.

Further, as the numbers of the supports 1 and the flat membranes 7 can respectively be adjusted, it is possible to vary the membrane area. For this reason, various amounts of treated liquid from a small amount to a large amount, are possible. However, from the viewpoint of preventing clogging and increasing the concentration efficiency, it is most preferred to flow the diffusion liquid past the pore diffusion flat membrane separation apparatus.

As described above, the flat membrane concentration apparatus of the present invention has succeeded in weight reduction of the apparatus as a whole and through the simplification of the apparatus construction and facilitated assembly and disassembly thereof, convening handling has been made possible.

With the present invention, component concentration under mild conditions is made possible. Further, in comparison with the conventional membrane concentration method, with the present invention; the followings can be made easily;

(1) continuous concentration with an operation with a low transmembrane pressure difference lower than 1 atm is made possible;

(2) respecting the component to be concentrated, a component such as a peptide, having a molecular weight of 500 or more, and respecting a component having a molecular weight of 1000 or more in particular, concentration of 10 times from low concentration from of 1% or less is made possible;

(3) increase in concentration on the membrane surface due to component having a molecular weight of 200 or less, such as an amino acid, is prevented and continuous concentration is made possible;

(4) the housing can be assembled, disassembled and reused;

(5) liquid flow on the concentrated side can be maintained uniform, thus maintaining the sanitary property; and (6) light weight with the possibility of varying the effective membrane area from 0.001 $m^2$ to 10 $m^2$.

[3] Regenerated Cellulose Porous Membrane

Next, there will be explained a regenerated cellulose porous membrane as a membrane mounted in the pore diffusion type flat membrane separation apparatus and a method of manufacturing such membrane. More particular, the explanation concerns a flat membrane optimum for the technique of separating and refining a target substance by diffusion of the substance through the pores in the porous membrane and its manufacturing method.

The regenerated cellulose porous membrane of the present invention comprises a multi-layered regenerated cellulose membrane including a porous structure having an average pore diameter (2rf) ranging from 5 to 500 nm, a membrane thickness (d) ranging from 50 to 500 μm, a porosity (Pr) ranging from 0.6 to 0.9; and a development degree of intermolecular hydrogen bond of 40% or less.

Preferably, the average pore diameter (2rf) ranges from 8 to 100 nm, the membrane thickness (d) ranges from 100 to 300 μm, and the product of the porosity (Pr) and the membrane thickness (d) is 50 μm or more.

More preferably, the product of the porosity (Pr) and the membrane thickness (d) ranges from 100 μm to 200 μm, This regenerated cellulose porous membrane is manufactured by the steps of forming a porous membrane by a micro-phase separation technique from a solution of cellulose ester as a cellulose derivative with addition of 1% in weight or more of a metal salt thereto; and subsequently subjecting the resultant membrane to a saponification treatment with an alkaline aqueous solution having a pH value ranging from 11 to 13 at a temperature of 50° C. or lower.

Preferably, the cellulose ester is cellulose acetate.

As the metal salt, a hydrochloride salt or acetate salt of an alkaline earth metal is suitable. Calcium chloride is particularly suitable.

Further preferably, the micro-phase separation method is caused by evaporation of good solvent of cellulose ester.

Cellulose acetate (polymerization degree 190) having an average substitution degree of 2.46 is dissolved in acetone such that the concentration in the flow casting solution may range from 3 to 13 weight percent. On the other hand, a mixed solution is prepared such that concentrations of methanol/$CaCl_2.2H_2O$/cyclohexanol in the flow casting solution may be 4-8% in weight/1-10% in weight/15-35% in weight, respectively. Then, these two solutions are completely dissolved in a dissolving machine which effects rotation and revolution in repetition, so that through degassing and filtration, thereby increasing the cleanliness degree to manufacture the flow casting solution.

Flow casing is effected on a glass plate in the thickness from 0.5 mm to 2 mm. And, mainly the good solvent (in this case, acetone) is evaporated so that a temperature difference of 10° C. or more will develop between the outside temperature and the temperature of the glass plate. In the course of this evaporation, there occurs a micro-phase separation, so that the flow casting solution becomes white. After 20 to 60 minutes, the flow-cast membrane manufactured and the glass plate are submerged in methanol, thereby to eliminate any solvent and calcium chloride remaining within the membrane.

Methanol present in the membrane is substituted with purified water and the membrane is submerged in caustic soda aqueous solution (pH=12) at 50° C. or lower and stirred occasionally, to allow a saponification reaction to take place for 20 hours, and then water-washed, whereby the inventive regenerated cellulose porous membrane is obtained. Then, as this porous membrane is supported to the flat plate-like support formed of polycarbonate, a pore diffusion type flat membrane separation apparatus is completed.

EXAMPLE 3

Degassing and filtration were carried out for a solution in which cellulose acetate (average polymerization degree 210)

having an average substitution degree of 2.50 was dissolved in a weight concentration (weight concentration in the flow casting stock solution) of 11.5% and a solution prepared with acetone: 51.6% in weight, methanol: 6.5% in weight, $CaCl_2 \cdot 2H_2O$: 1.2% in weight, cyclohexanol: 29.2% in weight, respectively.

Flow casting was effected on the glass plate to a flow casting thickness of 1 mm. Then, this was kept at 25° C. for 30 minutes to allow a micro-phase separation to occur. Thereafter, this was submerged together with the glass plate in methanol at 25° C., to stop further progress of the micro-phase separation. Then, components remaining in the membrane after the phase separation were eliminated by washing with purified water. This was submerged in 25° C. water adjusted to pH=12.0 with caustic soda to allow a saponification reaction to take place.

The regenerated cellulose porous membrane after the saponification reaction had a membrane thickness of 180 μm, an average pore diameter of 9.5 nm and a porosity of 0.82.

Further, by a method similar to the above, a regenerated cellulose porous membrane was manufactured. In this case, methanol was 15% in weight and cyclohexanol was 20.7% in weight and the resultant regenerated cellulose porous membrane had an average pore diameter of 40 nm and a porosity of 0.67.

The porous membrane thus obtained was dried and then its ultra-thin piece (membrane thickness 100 nm) after dyeing with osmium acid was observed for its cross section, under an electron microscope. As a result, there was observed a laminar structure having a thickness from 100 to 200 nm parallel with the membrane surface. FIG. 7 shows an 30,000 times magnified electron microscopic photography. In FIG. 7, the vertical direction is the thickness direction of the membrane. A laminar structure having from 1000 to 2000 layers was confirmed.

The regenerated cellulose porous membrane was mounted in a pore diffusion type flat membrane separation apparatus. With setting the effective membrane area to 100 $cm^2$, untreated liquid was flown on its surface (2 mL/min.) while purified water (diffusing liquid) was flow on the back side of the membrane. (flow rate: 3 mL/min.).

In order to render the transmembrane pressure difference substantially zero, cooperating pumps were provided at the inlet and outlet sides of the purified water side. As the treated liquid, commercially available milk was employed as it was. In the diffusing liquid, only the dissolved components present in the milk were effused and the particulate components were completely eliminated. The permeation ratio of protein was from 5 to 7%. Even when the amount of treated liquid was 5 L, substantially no reduction in the protein concentration in the diffusing liquid was observed.

The regenerated cellulose porous membrane of the present invention can be mounted in the pore diffusion type flat membrane separation apparatus and can achieve high microparticle eliminating performance. Needless to say, this membrane can be used also as a filtering membrane and it is easier for the inventive membrane to provide a higher virus preventing performance, in comparison with the conventional hollow fiber membrane for virus prevention.

For instance, with a flat membrane, its thickness can be set to 200 μm easily. Whereas, this is nearly impossible with a hollow fiber membrane. This difference of membrane thickness is related directly to the virus preventing performance. As the membrane alone can be replaced, it is also readily possible to reduce the cost of membrane module to ⅕ or less per unit treated liquid amount, as compared with the hollow fiber module.

Further, with the regenerated cellulose porous membrane of the present invention, clogging hardly occurs. Hence, this can serve in the microparticle eliminating technique in various industries and can serve also in the barrier membrane technique for keeping microparticles alone within a closed space, with the other molecules being present in an open space.

[4] Method of Non-Destructive Inspection of Flat Membrane

Next, there will be described a method of inspecting a microparticle eliminating membrane. This flat membrane inspecting method is a method of inspecting microparticle eliminating ability of a membrane having ability to eliminate microparticles such as prions, viruses, bacteria, etc., the method being a non-destructive inspection method allowing reuse of the membrane as a microparticle eliminating membrane after the implementation of this inspection method.

In order to allow reuse of a flat membrane having a plurality of pores and configured for separating a particular dispersed substance contained in a solution for separating a particular dispersed substance in a solution, the inventive method of non-destructive inspection of a flat membrane having a plurality of pores, the method comprising an integrity testing step for confirming particle eliminating ability of the flat membrane has not been reduced due to pore diffusion, by means of a direct method utilizing microparticles other than noble metals. The method further comprises a dissolving eliminating step for dissolving and eliminating the microparticles, after completion of the integrity test step.

FIG. 8 is an overall view of an integrity test apparatus for a pore diffusion type flat membrane separation apparatus (MDPM) 33.

Marks or numerals in the figure denote the followings:
21: a mount for mounting a set of the integrity test apparatus;
22: a mount for mounting an integrity test colloid particle; dispersion liquid (IS) and purified water (W), the mount 22 being vertically movable in unison with a mount 26;
23: a first stage mount (fixed);
24: a controller for an electric motor 25 for controlling the elevation of a second stage mount;
25: an electric motor 25 for lifting up/down the second stage mount 26;
26: the second stage mount vertically movable;
27: a base for supporting the mount 21;
28: a chain for moving the second stage mount 26, vertically movable by an electric motor;
29: a vessel for holding purified water (W);
30: a vessel for holding colloid particle dispersion liquid (IS);
31: a receiving vessel for the dispersion liquid;
32: a receiving vessel for liquid obtained from the colloid particle dispersion liquid after an integrity test:
33: a pore diffusion type flat membrane separation apparatus (MDPM);
34: an interlock liquid feeding pump for causing substance dispersion in the purified water (W);
35: a faucet for regulating flow rate of the colloid particle dispersion liquid (IS);
36: a transport tube for purified water (W) for dispersing substance (collection target substance) diffused through pores;

37: a tube for diffusion collection of target substance; and
38: a communication cylinder having virus eliminating ability and configured for communicating the vessel 29 with the outer atmosphere.

There will be described a best mode of embodying the present invention, in the case of using a flat membrane (membrane area: 100 cm$^2$) comprised of a regenerated cellulose porous membrane having an average pore diameter of 30 nm (porosity: 68%, membrane thickness: 170 microns, an example of hydrophilic polymer) for a globulin (molecular weight: about 400,000) aqueous solution (concentration: 1% in weight).

The globulin aqueous solution is put in the vessel 30 and purified water is put in the vessel 29. The interlock pump 34 is operated to charge the pore diffusion flat membrane separation apparatus 33 with the purified water and the flow rate to be provided by the pump 34 is set to 2 mL/min. And, the flow rate adjusting faucet 35 is operated to set so that the globulin aqueous solution may flow at 1 mL/min. The flow amount is set such that the globulin concentration of the globulin aqueous solution in the receiving vessel 32 may range from 50 to 90% of the concentration in the vessel 30.

After 10 L of the globulin aqueous solution is treated by the pore diffusion type flat membrane separation apparatus 33, with using the pump 34, the flat membrane inside the pore diffusion flat membrane separation apparatus 33 is reverse-washed with purified water contained inside the vessel 29.

As an aqueous solution for integrity test by the direct method, an aqueous solution containing ferric hydroxide colloid particles having a particle diameter of 30 nm, polyvinyl alcohol as a stabilizing agent, and a cation surfactant agent is selected and this was charged into the vessel 30 and then the faucet 35 is fastened. After the pump 34 is operated to flow 100 mL of purified water, the pump 34 was stopped. After the pump was kept stopped for 10 minutes, the pump 34 is operated again to sample the testing liquid within a circuit 36 and the iron concentration in this liquid is determined. From the determined iron concentration of the aqueous solution in the vessel 30, a microparticle logarithmic reduction factor $\Phi$ is calculated by the following Mathematical Formula 7.

$$\Phi = \log Co/Cd \qquad \text{[Mathematical Formula 7]}$$

(Co: concentration of iron in aqueous solution in vessel 10, Cd: concentration of iron in aqueous solution in circuit 16).

For the iron concentration determination, ferric hydroxide in the liquid is ionized and this is colored by a complex forming technique and the resultant liquid is subjected to determination by a spectroscope to obtain an absorbance. As both Co and Cd vary in proportion with the absorbance, $\Phi$ can be determined. If the value of $\Phi$ is greater than a preset value, then, it can be confirmed that the used membrane retains its microparticle eliminating ability. Specifically, in the above case, $\Phi$ is greater than 3.

After an integrity test, as a dissolving eliminating liquid, hydrochloric acid having a normality value of 0.2 is charged into the vessels 29, 30, thereby to convert the entire aqueous solution present in the pore diffusion flat membrane separation apparatus 33 to this dissolving eliminating liquid. After one hour, purified water is charged into the vessels 29, 30 to adjust the pH value of the aqueous solution to 1.0 and the pore diffusion flat membrane separation apparatus 33 is filled with this aqueous solution.

After being left for 12 hours, purified water is charged into the vessels 29, 30 and with using the faucet 35 and the interlock pump 34, the aqueous solution present inside the pore diffusion type flat membrane separation apparatus 33 is replaced by purified water. The pore diffusion type flat membrane separation apparatus 33 is reused as a membrane for eliminating microparticle from the globulin aqueous solution.

Inside the pore diffusion flat membrane separation apparatus after the dissolving eliminating treatment subsequent to the integrity test, no ferric hydroxide colloid particles remain. However, if there is a need for applying the pore diffusion flat membrane separation apparatus to an aqueous solution of other substance, then, the following steps may be added before or after the integrity test.

That is, (A) perchloric acid aqueous solution is charged into the MDPM, and after one hour, (B) dissolving elimination is carried out with an aqueous solution containing a surfactant, and then, (C) sodium hydroxide aqueous solution is added to obtain aqueous solution having a normality value of 0.1 and the resultant solution is charged into the MDPM. After 10 hours, (D) the inside of the MDPM is replaced by purified water; (E) further, the purified water is replaced by sodium hydroxide aqueous solution having a normality value of 0.1. In case the pore diffusion flat membrane separation apparatus is constructed as an assembled type, the flat membrane and the housing are disassembled from other and are stored as they are until their reuse. (F) Prior to reuse, hydrochloric acid aqueous solution having a normality value of 0.1 is introduced into the pore diffusion flat membrane separation apparatus 33 to neutralize the sodium hydroxide aqueous solution; and further (G) MDPM is subjected to a dissolving eliminating treatment with purified water.

EXAMPLE 4-1

Eel was digested with a proteinase ("Thermoase PC-10", manufactured by Daiwa Fine Chemicals Co., Ltd.); then, the aqueous solution components were collected by centrifugal separation. About 2 L of the resultant aqueous solution was subjected to separation by the pore diffusion technique using a pore diffusion type flat membrane separation apparatus (having a housing formed of polycarbonate) comprised of a regenerated cellulose porous membrane having an average pore diameter of 25 nm, a porosity of 65% and a membrane thickness of 180 microns.

The effective diffusion area was 100 cm$^2$.

The principal components in the diffusion liquid were peptides and amino acids and it was found that the enzyme was remaining in the diffusion liquid.

The pore diffusion flat membrane separation apparatus after the use was set as shown in FIG. 8. Purified water was charged in the vessel 29 and in the vessel 30, there was charged an aqueous solution (IS) containing ferric hydroxide colloid particles (0.02% in weight) having an average particle diameter of 25 nm, polyvinyl alcohol (0.01% in weight) and cation surfactant (1% in weight, "Cation AB" manufactured by NOF Corporation).

The interlock pump 34 was operated to charge purified water into the pore diffusion type flat membrane separation apparatus 33. The flow rate controlling faucet 35 was opened to charge the above aqueous solution IS into the pore diffusion flat membrane separation apparatus 33 and then the faucet 35 was closed. After 10 minutes, the interlock pump 34 was operated to collect the diffusion liquid.

Iron in the above aqueous solution IS and the concentration of iron in the diffusion liquid were determined. Specifically, hydrochloric acid was added to each liquid to adjust to pH=1.0 and the resultant liquid was heated to 50° C. for 10 minutes and a trace amount of potassium thiocyanate was added for coloring.

The absorbance of this solution was determined by a spectroscopy. As the result, it was found that the value of Φ calculated by Mathematical Formula 3 was greater than 3. The vessel 10 was filled with hydrochloric acid aqueous solution having a normality value of 1. The interlock pump 34 provided at the inlet side of the pore diffusion flat membrane separation apparatus was operated to effect dissolution elimination with the above hydrochloric acid aqueous solution. Immediately thereafter, the pore diffusion flat membrane apparatus 33 was removed from the circuit and this pore diffusion flat membrane apparatus 33 was entirely submerged in NaOH aqueous solution having a normality value of 0.1.

The pore diffusion flat membrane apparatus 33 as being kept under the submerged condition, was disassembled into the flat membranes and the housing. The housing constituting the module was water-washed and then heated and dried at 110° C. The flat membrane was kept submerged in the NaOH aqueous solution of 0.1 normality for 2 days and then water-washed. The water-washed flat membranes were assembled again to make up the pore diffusion type flat membrane separation apparatus 33.

Thereafter, in a pore diffusion test similar to the above, the regenerated pore diffusion flat membrane separation apparatus 33 was used. This regenerating operation was repeated five times, but there occurred no change in the pore diffusion characteristics.

In the membrane separation technique for microparticle elimination, there is an obligation imposed for an integrity test on a used membrane. With the conventional art, as this integrity test was a destructive test, there was no possibility of reuse of the membrane if this text is conducted. The integrity test proposed by the present invention has provided the possibility of reuse of a membrane after this test.

In particular, the combination with the pore diffusion technique has made the reuse of membrane possible. The invention allows application of the direct method to the integrity test even for a flat membrane. So that, the need for dissolution elimination of components adhered to the flat membrane can be reduced, and the costs required for integrity test can be reduced also. That is, as the microparticles used in the direct method in the present invention are microparticles other than noble metals, so the preparation thereof is easy and inexpensive.

EXAMPLE 4-2

Membrane was formed by the casting method from an acetone solution of cellulose acetate and then the resultant membrane was subjected to a saponification treatment, thus manufacturing a regenerated cellulose porous membrane (average pore diameter: 9 nm, porosity: 85%, membrane thickness: 160 microns). The microparticle eliminating ability of this membrane was evaluated by the pore diffusion method with a ferric hydroxide colloid particle dispersion liquid having an average pore diameter of 20 nm.

The dispersion liquid mixedly contained therein polyvinyl alcohol and non-ionic surfactant. The particle logarithmic removal factor was greater than 4.5. The membrane after the eliminating ability test was submerged for 3 hours in a hydrochloric acid aqueous solution having normality value of 1 and at 40° C. In order to confirm the ferric hydroxide on the membrane surface had been completely dissolved and eliminated, the membrane was submerged in hydrochloric acid having normality value of 1 and at 40° C. and potassium thiocyanate was added thereto and the iron concentration in the aqueous solution was determined by a spectral photometer. The membrane after the confirmation was washed with purified water.

The membrane after the washing was employed for treating 1% globulin aqueous solution by the pore diffusion method, for 500 liters per 1 $m^2$ of membrane area. Thereafter, an integrity test was conducted by the pore diffusion method with the same ferric hydroxide colloid particle dispersion liquid as the above-described performance test. Then, it was found that the particle logarithmic prevention efficient was greater than 4.5.

After the integrity test, the membrane was kept submerged for 24 hours at the room temperature in hydrochloric acid aqueous solution having normality value of 1. Next, the membrane was submerged for 48 hours in a caustic soda solution having a normality value of 0.15 and then water-washed. It was found that the transmembrane pressure difference of the filtering speed (0.15 atm.) of the membrane after the water washing completely agreed with that before the use.

EXAMPLE 4-3

After mixture (mole ratio: 1:2) of 0.0045 mol/L of ferric chloride and ferrous chloride was dissolved in water, polyvinyl alcohol having a polymerization degree of 500 was dissolved to a concentration of 0.01% in weight. To this, a cation surfactant ("Cation AB" manufactured by NOF Corporation) was mixed to a concentration of 2% in weight. And, this was heated at 75° C., thereby manufacturing dispersion liquid of ferric hydroxide colloid particles having an average particle diameter of 20 nm.

On the other hand, the micro-phase separation method and the saponification method were employed to manufacture a regenerated cellulose flat membrane having an average pore diameter of 25 nm, a porosity of 80% and a membrane thickness of 80 microns. On this membrane, particle eliminating ability thereof was determined by the pore diffusion method, with using ferric hydroxide colloid particles having a pore diameter of 20 nm. Then, it was found that the logarithmic removal factor was greater than 5.

Immediately after its test, the membrane was submerged in a hydrochloric acid aqueous solution having a normality value of 0.2, at 30° C. for 1 hour, thereby dissolving and eliminating any remaining ferric hydroxide colloid particles.

The membrane after the dissolution elimination was used for treating, by the pore diffusion method, 3% in weight of gammagloblin aqueous solution at the rate of 500 L/$cm^2$. Thereafter, the integrity test by the pore diffusion method was conducted, with using the above-described colloid particle dispersion liquid.

The particle logarithmic removal factor was found to be greater than 5. The membrane after the integrity test was submerged in 0.1 normality caustic soda aqueous solution.

The determination of concentration of ferric hydroxide was carried out in the manner as follows. First, the test liquid was rendered to the composition of the 0.5 normality hydrochloric acid aqueous solution and stirred at 50° C. for 30 minutes, thereby rendering the ferric hydroxide into a trivalent iron ions, and to this, potassium thiocyanate was added. Then, on this, by determining absorbance at a wavelength of 480 nm with a spectral photometer, the concentration was determined.

With the present invention, there has been established the possibility of reuse of a flat membrane even after implementation of an integrity test using a microparticle eliminating membrane. In particular, with the microparticle eliminating membrane for the pore diffusion method, the invention provides the possibility of reusing the flat membrane after the integrity test.

INDUSTRIAL APPLICABILITY

The pore diffusion type flat membrane separation apparatus according to the present invention will find applications in such industries in which separation and refinement under mild conditions are required (e.g. pharmaceutical companies and food stuff industry), for separation, refinement of a substance having a biological activity such as a protein. Further, the invention may be incorporated in an industrial process as a method of refining/separating particular microparticles including colloid particles, in an industry handling colloidal particles. Especially, the invention is suitably used for allowing long-term use of a flat membrane having a high virus removability.

The flat membrane concentration apparatus according to the present invention can be used, in a manufacturing process of biomedical products, for concentrating a component in a dispersion liquid on which microparticle elimination has been conducted by the pore diffusion type flat membrane separation apparatus. In the membrane concentration of this flat membrane concentration apparatus, a substance having a target molecular weight can be concentrated, without increase in the concentration of water-soluble metal salts therein.

The regenerated cellulose porous membrane according to the present invention may be used as being mounted in the pore diffusion type flat membrane separation apparatus and can achieve high microparticle eliminating performance. Further, as clogging phenomenon hardly occurs with this regenerated cellulose porous membrane, this can serve, in may industries, as a microparticle eliminating technique, and a barrier membrane technique for keeping microparticles alone within a closed space, with keeping the other molecules in an open space.

The method of non-destructive inspection of a flat membrane according to the present invention may be utilized in a method of inspecting a microparticle eliminating ability of a membrane having ability to eliminate microparticles such as prions, viruses, bacteria, etc.

DESCRIPTION OF REFERENCE MARKS

Figure 1:
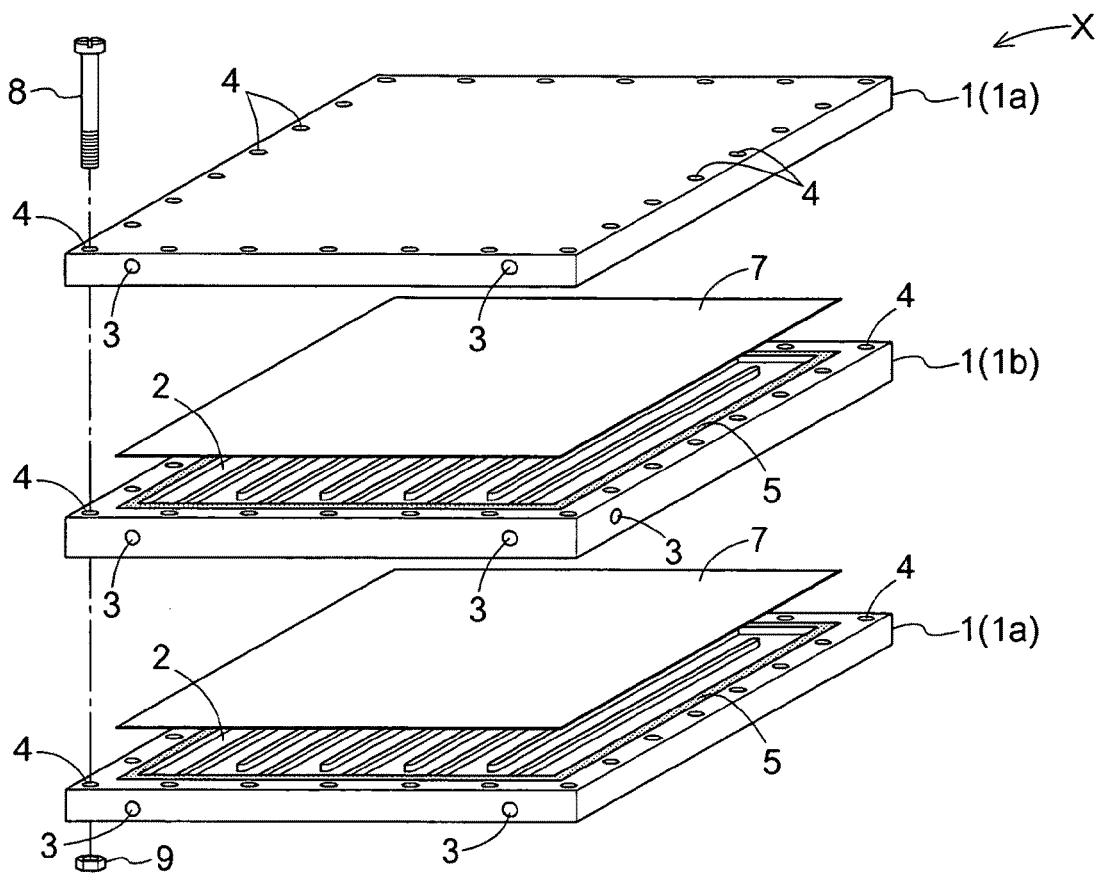
FIG. 1 a schematic view showing a pore diffusion type flat membrane separation apparatus according to the present invention, FIG. 2 a schematic plain view of a flat membrane, FIG. 3 a schematic view in cross section of the pore diffusion type flat membrane separation apparatus, FIG. 4 a schematic view of a flat membrane concentration apparatus according to the present invention, FIG. 5 a schematic cross section of the flat membrane concentration apparatus, FIG. 6 a schematic plain view of a support, FIG. 7 a view showing an electron-microscopy (30,000 times magnification) of a membrane section of a regenerated cellulose porous membrane, FIG. 8 an overall view of an integrity test apparatus, FIG. 9 a view schematically showing, in section, of a membrane used in pore diffusion taken parallel with the planar membrane surface, FIG. 10 a view schematically illustrating pore diffusion technique, FIG. 11 a graph showing relationship between residence period and concentration respectively of a treating liquid and a diffusion liquid, and FIG. 12 a graph showing relationship between a collection ratio and a flow amount.
Figure 2:
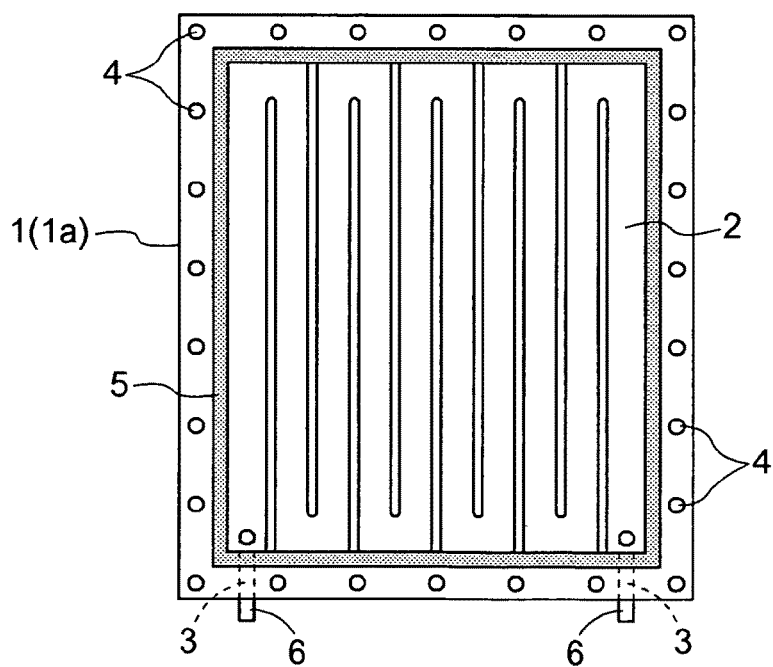
Figure 3:
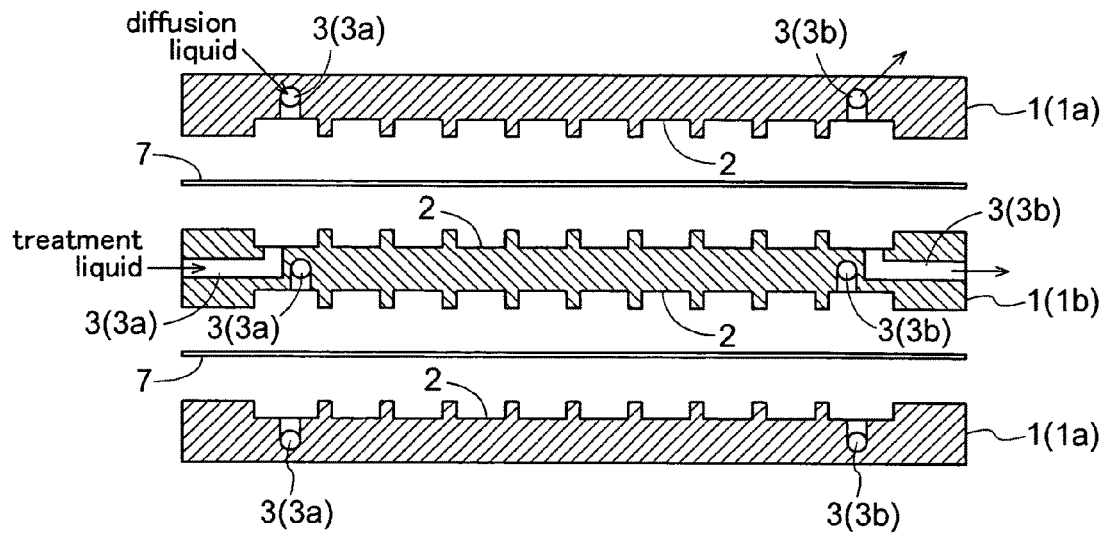
Figure 4:
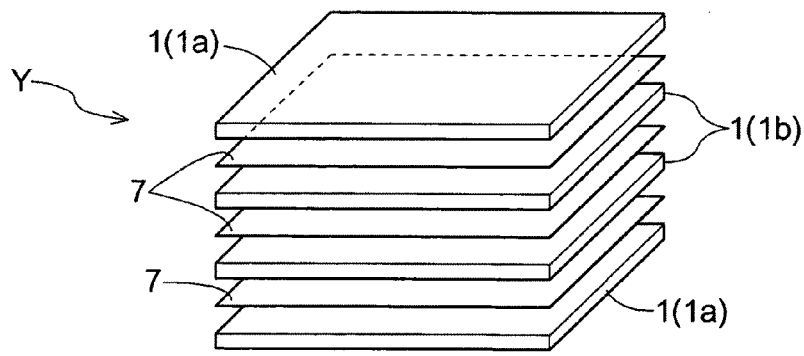
Figure 5:
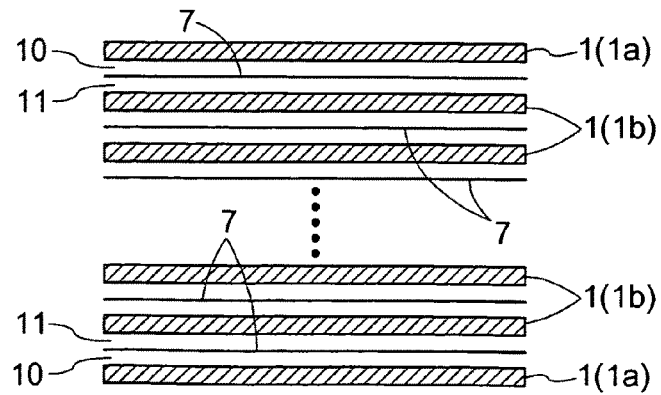
Figure 6:
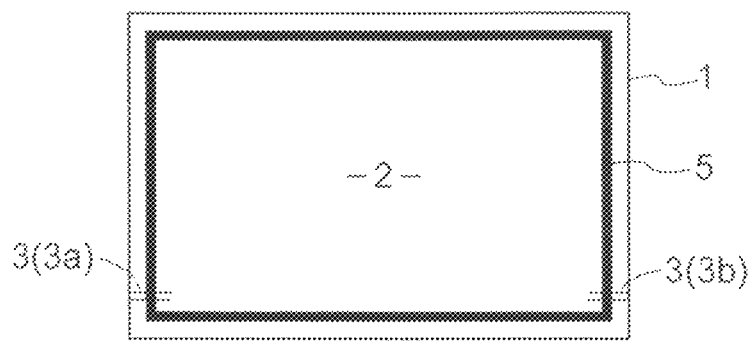
Figure 7:
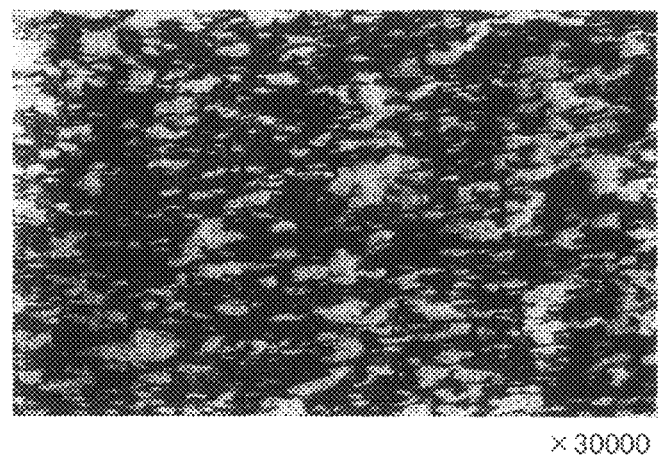
Figure 8:
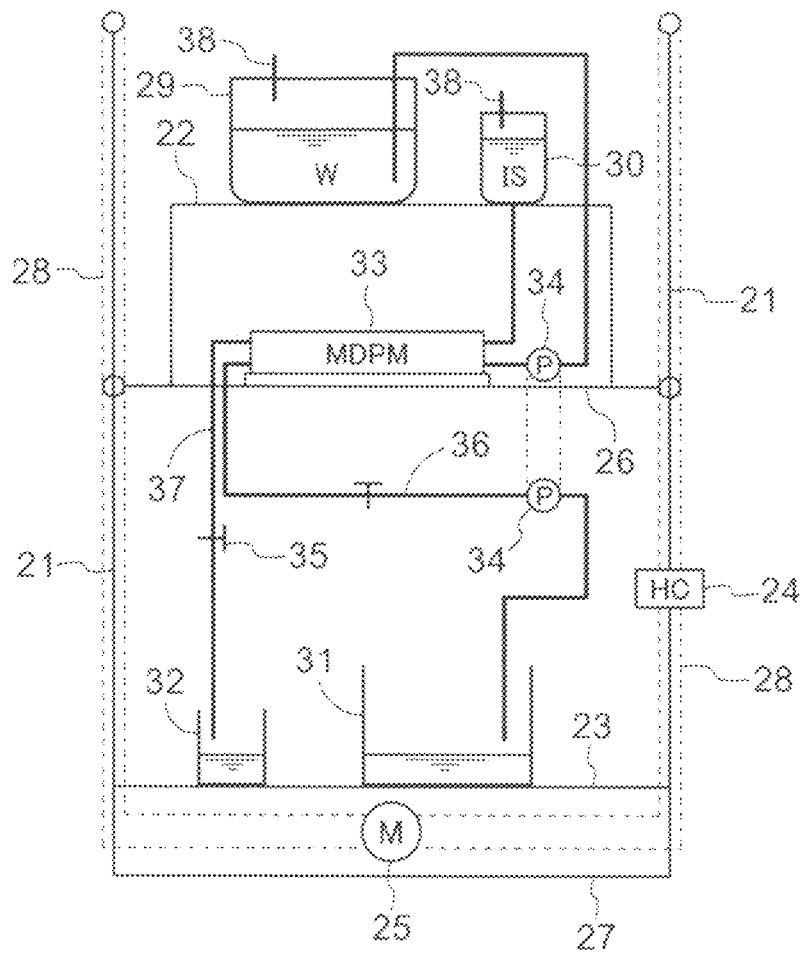
Figure 9:
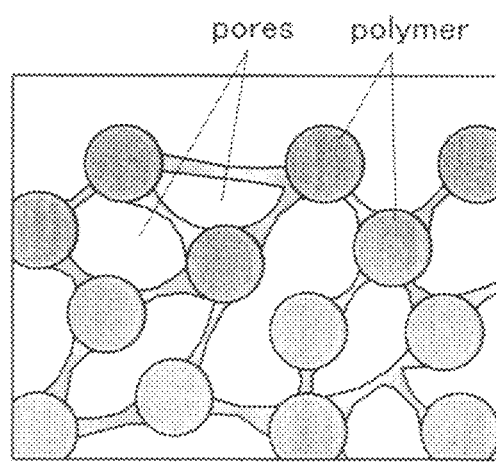
Figure 10:
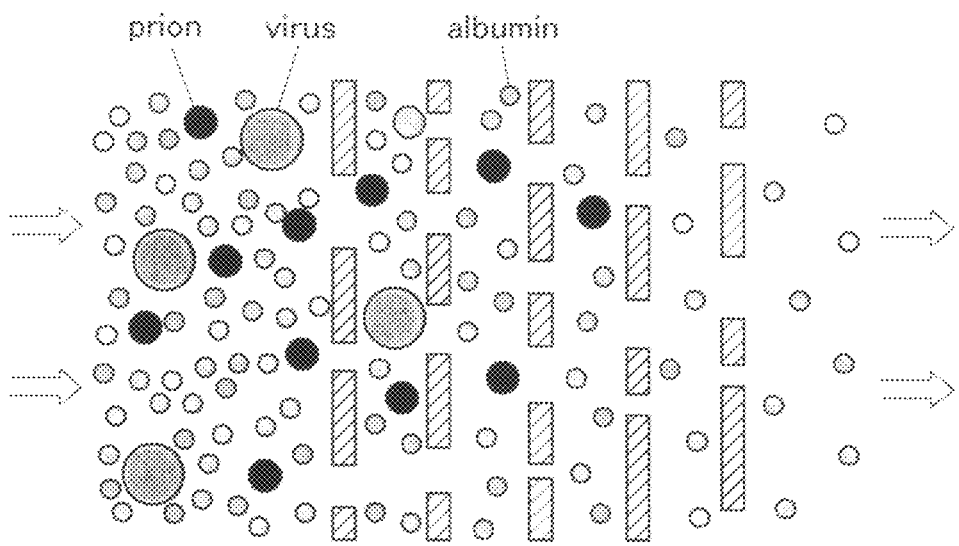
Figure 11:
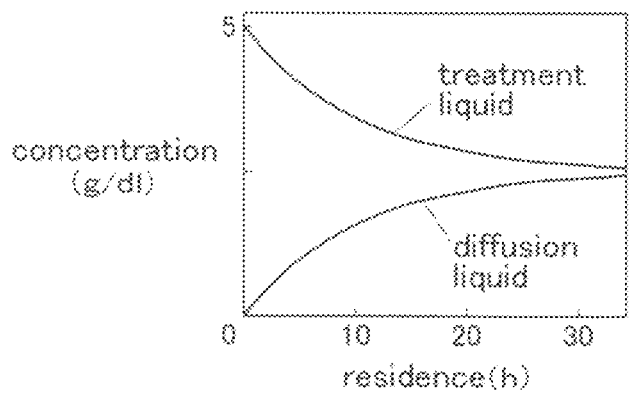
Figure 12:
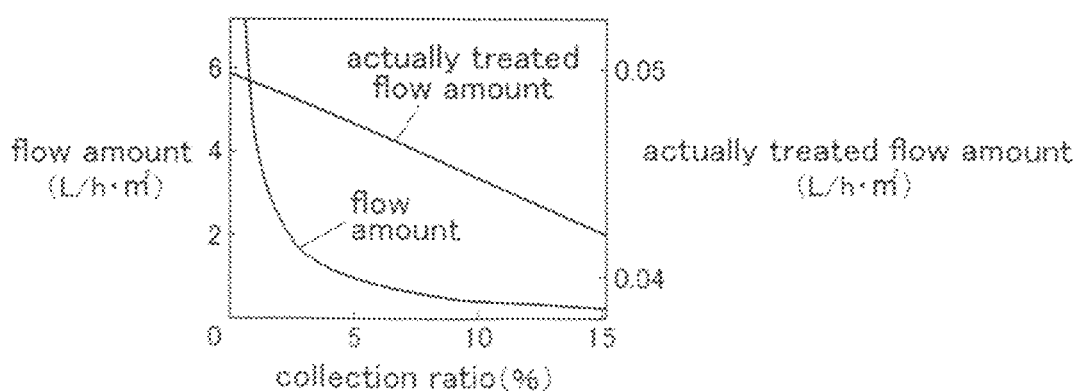

X pore diffusion type flat membrane separation apparatus,
1 flat plate-like support,
2 flow conduit
3 water conduit
7 flat membrane.

The invention claimed is:

1. A pore diffusion type flat membrane separation apparatus comprising:
   a plurality of flat membranes; and
   a plurality of flat plate-like supports arranged alternately with the plurality of flat membranes,
      each flat membrane defining a plurality of pores and separating a predetermined dispersed substance contained in a solution by a pore diffusion technique where substantially no transmembrane pressure difference is applied, and
      each flat plate-like support having a flow conduit on one or both faces thereof, wherein
   an average pore diameter of each flat membrane is set from 5 nm to 500 nm, and a porosity of each flat membrane is set from 0.6 to 0.9;
   a ratio between a spatial volume of any flow conduit and a membrane area of a corresponding flat membrane is set from 0.04 to 0.4 cm;
   each flat plate-like support includes, in at least two positions in lateral faces thereof, water conduits in communication with a flow conduit, so that flow directions of said solution in flow conduits of upper and lower flat plate-like supports separated by a flat membrane may be substantially in the same direction;
   a treatment liquid subjected to a diffusion treatment is caused to flow under a flat membrane and a diffusion liquid in which a dispersed substance flows is caused to flow on and upwardly of a flat membrane;
   an outer side flat plate-like support includes a flow conduit in one face thereof, a water conduit on an inlet side, and a water conduit on an outlet side both in communication with a flow conduit in a lateral face of the outer side flat plate-like support;
   at least one intermediate flat plate-like support includes flow conduits in both faces thereof,
      the flow conduit in one face being in communication with an inlet side water conduit where treatment liquid flows in and an outlet side water conduit where the treatment liquid flows out,
      the flow conduit in the other face being in communication with an inlet side water conduit where the diffusion liquid flows in and outlet side water conduit where the diffusion liquid flows out, and
      the treatment liquid-inlet side water conduit, the treatment liquid-outlet side water conduit, the diffusion liquid-inlet side water conduit, and the diffusion liquid-outlet side water conduit being provided in the lateral face of the at least one intermediate flat plate-like support; and
   said plurality of flat plate-like supports and said plurality of flat membranes can be assembled with and disassembled from each other.

2. The pore diffusion type flat membrane separation apparatus according to claim 1, wherein
a packing formed of a polymer elastic member is provided in a peripheral portion of at least one of an upper and lower face of any flat plate-like support.

3. The pore diffusion type flat membrane separation apparatus according to claim 1, wherein
each flat plate-like support is formed of a material exhibiting characteristics of heat resistance, shock resistance, alkali resistance, acid resistance, light weightiness and transparency, the material being selected from the group consisting of polycarbonate, polyamide, polyacetal, polysulphone, polyether sulphone, and polyether ether sulphone.

4. The pore diffusion type flat membrane separation apparatus according to claim 2, wherein
each flat plate-like support is formed of a material exhibiting characteristics of heat resistance, shock resistance, alkali resistance, acid resistance, light weight weightiness and transparency, the material being selected from the group consisting of polycarbonate, polyamide, polyacetal, polysulphone, polyether sulphone, and polyether ether sulphone.

5. The pore diffusion type flat membrane separation apparatus according to claim 1, wherein
for each flat membrane, a development degree of an intermolecular hydrogen bond is set to 40% or less.

* * * * *